(12) United States Patent
Millet, Jr. et al.

(10) Patent No.: US 10,890,591 B2
(45) Date of Patent: *Jan. 12, 2021

(54) METHODS AND DOSE PACKS FOR MONITORING MEDICATION ADHERENCE

(71) Applicant: Synapse Biosciences, LLC, Raleigh, NC (US)

(72) Inventors: Robert Anthony Millet, Jr., Hillsborough, NC (US); Philip T. Radford, Wake Forest, NC (US); Ashwin Anand Patkar, Cary, NC (US)

(73) Assignee: Synapse Biosciences, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/167,993

(22) Filed: Oct. 23, 2018

(65) Prior Publication Data

US 2019/0056414 A1    Feb. 21, 2019

Related U.S. Application Data

(63) Continuation of application No. 15/585,773, filed on May 3, 2017, now Pat. No. 10,145,855.

(60) Provisional application No. 62/331,393, filed on May 3, 2016, provisional application No. 62/360,436, filed on Jul. 10, 2016.

(51) Int. Cl.
| | | |
|---|---|---|
| *G01N 33/94* | (2006.01) | |
| *G01N 33/493* | (2006.01) | |
| *C07D 307/00* | (2006.01) | |
| *C07D 277/00* | (2006.01) | |
| *A61K 31/10* | (2006.01) | |
| *A61K 31/075* | (2006.01) | |
| *A61K 31/13* | (2006.01) | |
| *A61B 5/00* | (2006.01) | |

(52) U.S. Cl.
CPC ........... *G01N 33/94* (2013.01); *G01N 33/493* (2013.01); *A61B 5/00* (2013.01); *A61K 31/075* (2013.01); *A61K 31/10* (2013.01); *A61K 31/13* (2013.01); *C07D 277/00* (2013.01); *C07D 307/00* (2013.01); *G01N 2560/00* (2013.01); *G01N 2800/52* (2013.01)

(58) Field of Classification Search
CPC ........ A61B 5/00; A61K 31/075; A61K 31/10; A61K 31/13; C07D 277/00; C07D 307/00; G01N 2560/00; G01N 2800/52; G01N 33/493; G01N 33/94
See application file for complete search history.

(56) References Cited

U.S. PATENT DOCUMENTS

| | | |
|---|---|---|
| 5,776,783 A | 7/1998 | Kell |
| 6,068,981 A | 5/2000 | Rittenburg et al. |
| 6,136,801 A | 10/2000 | Kell |
| 2003/0044457 A1* | 3/2003 | Faour ............... A61K 9/0004 424/458 |
| 2005/0233459 A1 | 10/2005 | Melker et al. |
| 2007/0224128 A1* | 9/2007 | Dennis ............. A61B 5/4839 424/10.1 |
| 2010/0316639 A1 | 12/2010 | Lackner |
| 2011/0129433 A1 | 6/2011 | Currie |
| 2014/0057304 A1* | 2/2014 | Hryhorenko ....... C07K 16/44 435/7.93 |
| 2017/0074857 A1 | 3/2017 | Dennis et al. |

FOREIGN PATENT DOCUMENTS

| | | |
|---|---|---|
| DE | 3709575 | 10/1988 |
| WO | 2015134390 | 9/2015 |

OTHER PUBLICATIONS

Sato et al (Psychopharmacology, EPub Jul. 7, 2015, vol. 232, pp. 3497-3505) (Year: 2015).*
Webster et al (British Journal of Clinical Pharmacology, 1981, vol. 11, pp. 333-338) (Year: 1981).*
Farmer, K. (1999), "Methods for measuring and monitoring medication regimen adherence in clinical trials and clinical practice," Clinical Therapeutics, 21(6), 1074-1090.
Kapur, S., Ganguli, R., Ulrich, R., Raghu, U. (1991), "Use of random-sequence riboflavin as a marker of medication compliance in chronic schizophrenics," Schizophr Res., 6(1), 49-53.
Patkar, A., Millet, R., Leuth, E., Radford, P. (2014), "Urinary concentrations of buprenorphine and norbuprenorphine as indicators of noncompliance and diversion [abstract]." In: American Society of Addiction Medicine Annual Meeting, Apr. 23-26, 2015, Austin, Texas.
Shiovitz, T., Bain, E., McCann, D., Skolnick, P., Laughren, T., Hanina, A., Burch, D. (2016), "Mitigating the effects of nonadherence in clinical trials," J Clin Pharmacol, 56(9), 1151-1164.
Bötttcher M1, Beck O. Evaluation of buprenorphine CEDIA assay versus GC-MS and ELISA using urine samples from patients in substitution treatment J Anal Toxicol. Nov.-Dec. 2005;29(8):769-76.
Fareed A, Eilender P, Ketchen B, Buchanan-Cummings AM, Scheinberg K, Crampton K, Nash A, Shongo-Hiango H, Drexler K Factors affecting noncompliance with buprenorphine maintenance treatment. J Addict Med. Sep.-Oct. 2014;8(5):345-50.
Lofwall MR, Martin J, Tierney M, Fatséas M, Auriacombe M, Lintzeris N Buprenorphine diversion and misuse in outpatient practice. J Addict Med. Sep.-Oct. 2014;8(5):327-32.

(Continued)

*Primary Examiner* — Mark V Stevens
(74) *Attorney, Agent, or Firm* — Quarles & Brady LLP

(57) ABSTRACT

Provided herein are methods and dose packs for the monitoring of medication adherence. In one aspect, the dose pack comprises comprise a multiplicity of doses of an agent and a multiplicity of doses of a marker and be configured to isolate a pair of at least one of the multiplicity of doses of the agent and at least one of the multiplicity of doses of the marker for co-administration of the pair to the subject according to the dosing schedule. In another aspect, the method comprises obtaining a sample from the subject subsequent to the conclusion of a monitoring window and analyzing the sample for the presence or absence of a marker or a degradation product thereof.

15 Claims, 8 Drawing Sheets

(56) References Cited

OTHER PUBLICATIONS

Zosel A, et al. (2013), "Characterization of adolescent prescription drug abuse and misuse using the Researched Abuse Diversion and Addiction-related Surveillance (RADARS(®)) System," J Am Acad Child Adolesc Psychiatry, Feb. 52(2):196-204.
Babalopnis S, et al. (2015), "Quinine as a potential tracer for medication adherence: A pharmacokinetic and pharmacodynamic assessment of quinine alone and in combination with oxycodone in humans," J Clin Pharmacol, Dec. 55(12): 1332-43.
Hampson, Aidan J., et al. (2016), "A Pharmacokinetic Study Examining Acetazolamide as a Novel Adherence Marker for Clinical Trials," J Clin Psychopharmacol, 36: 324-332.
Ramanujam, V.M. Sadagopa, et al. (2011), "Riboflavin as an Oral Tracer for Monitoring Compliance in Clinical Research1," Open Biomark J, (4): 1-7.
Fox, S, (2010), "Urinary Riboflavin Needs Quantitative Measurement to Assess Adherence," Medscape, Dec. 6, 2010.
Lam, Wai Yin and Fresco, Paula, (2015), "Medication Adherence Measures: An Overview," BioMed Research International, 1-12.
International Search Report and Written Opinion of the International Searching Authority for PCT/US2017/030790 filed May 3, 2017.

* cited by examiner

|   | 1 | 2 | 3 | 4 | 5 | 6 | 7 |   |
|---|---|---|---|---|---|---|---|---|
|   | $M_1$ | $M_2$ | $M_3$ | $M_4$ | $M_5$ | $M_6$ | $M_7$ |   |
| $M_1$ | X | 0 | 0 | 0 | 0 | 0 | 0 | Y |
| $M_2$ | 0 | X | 0 | 0 | 0 | 0 | 0 | Y |
| $M_3$ | 0 | 0 | X | 0 | 0 | 0 | 0 | Y |
| $M_4$ | 0 | 0 | 0 | X | 0 | 0 | 0 | Y |
| $M_5$ | 0 | 0 | 0 | 0 | X | 0 | 0 | Y |
| $M_6$ | 0 | 0 | 0 | 0 | 0 | X | 0 | Y |
| $M_7$ | 0 | 0 | 0 | 0 | 0 | 0 | X | Y |

Fig. 6A

|  | 1 | 2 | 3 | 4 | 5 | 6 | 7 | |
|---|---|---|---|---|---|---|---|---|
|  | $M_1$ | $M_2$ | $M_3$ | $M_4$ | $M_5$ | $M_6$ | $M_7$ | |
| $M_1$ | X | 0 | 0 | 0 | 0 | 0 | 0 | Y |
| $M_2$ | 0 | 0 | 0 | 0 | 0 | 0 | 0 | < |
| $M_3$ | 0 | 0 | X | 0 | 0 | 0 | 0 | Y |
| $M_4$ | 0 | 0 | 0 | X | 0 | 0 | 0 | Y |
| $M_5$ | 0 | 0 | 0 | 0 | X | 0 | 0 | Y |
| $M_6$ | 0 | 0 | 0 | 0 | 0 | Z | 0 | > |
| $M_7$ | 0 | 0 | 0 | 0 | 0 | 0 | X | Y |

Fig. 6B

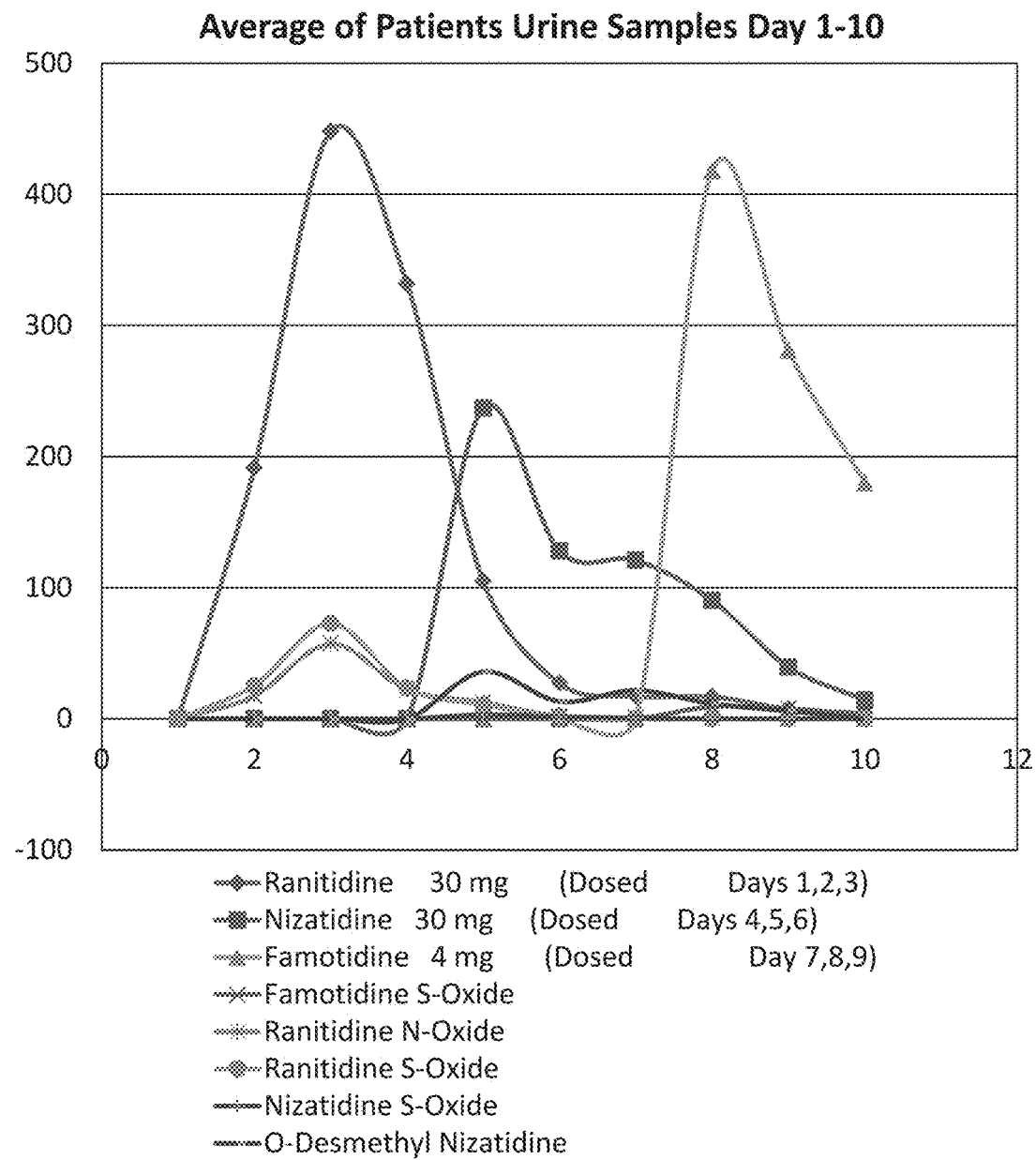

METHODS AND DOSE PACKS FOR MONITORING MEDICATION ADHERENCE

CROSS-REFERENCE TO RELATED APPLICATIONS

The present application is a continuation of U.S. patent application Ser. No. 15/585,773, filed May 3, 2017, which claims priority benefit to U.S. Provisional Application Ser. No. 62/331,393, filed 3 May 2016, and U.S. Provisional Application Ser. No. 62/360,436, filed 10 Jul. 2016, the contents of each are incorporated herein by reference in their entireties.

FIELD OF USE

The present disclosure relates generally to methods and dose packs for monitoring medication adherence. More specifically the present disclosure relates to methods of using markers, including histamine receptor ligands, and dose packs comprising the same for co-administration with agents to monitor adherence to a dosing schedule.

BACKGROUND

Adherence with prescribed medications in clinical practice as well as clinical trials is critical to the success of pharmacological interventions. In psychiatric disorders, clinical non-adherence rates range from 30-60%. Non-adherence is also a significant issue for elderly people with chronic diseases and becomes amplified when they have dementia associated with Alzheimer's disease (AD) and comorbid conditions such as cardiovascular disease. Beyond clinical practice, the issue of incomplete or sub-optimal adherence in clinical trials creates even greater problems in measuring efficacy of drugs where a significant placebo effect can complicate the measurement of efficacy.

Accurate measurement of adherence is particularly valuable in Phase II proof of concept trials where critical decisions about further clinical development of drugs need to be made. Non-adherence with the prescribed medication gives rise to unintended variability in actual drug exposure and introduces potentially powerful confounding effects in measurement of treatment effect. These issues with sub-optimal compliance indicate that mechanisms to accurately measure compliance during both clinical trials and during routine use of drugs could have a significant impact on the ability to prospectively exclude non-compliant patients in clinical trials or to assist caregivers in identification of non-compliant patients who are treated on an outpatient basis.

Adherence measurement tools typically are characterized as subjective (e.g., patient and/or caregiver recall of doses taken or missed) or objective (e.g. pill counts, direct observation, pharmacy refill records). Most evidence indicates that self-report adherence measures show only moderate correspondence to other adherence measures.

Objective compliance measures, such as pill counts and prescription refill history, are considered to be more valid, more reliable, and less influenced by social desirability and patient recall errors. However, these objective tools can be expensive and difficult to use correctly and may overestimate nonadherence. Electronic monitoring devices such as Medication Event Monitoring System (MEMS®) or Helping Hand® provide an objective measure with a microchip in the bottle or pill pack that prompts the patient to take the medication and stamps the time and date when the tablet was removed from the bottle or blister pack. Recent technological advances have also led to smartphones being employed to photograph or video record pill counts. Researchers have also developed ingestible biosensor system comprising a radio-frequency identification (RFID)-tagged gelatin capsule. Once the capsule dissolves in the stomach, the RFID tag activates to transmit a unique signal to a relay device which transmits a time-stamped message to a cloud-based server that functions as a direct measure of medication adherence (myTmed®). Furthermore, a constellation of mobile technologies that provide real-time direct measures of medication adherence have been developed including microchips being embedded in the capsule that communicate with a wearable device (Proteus or e-Tect®), facial recognition technology through smart phone (Aicure) and breath detection of a capsule tracer (Xhale Smart®). While these devices are more accurate than self-reports or pill counts, they are very expensive, require extensive subject training and compliance with technology, can raise subject anxiety and have the potential of increasing placebo response due to increased attention and 'halo effect' of the technology. Moreover many of these methods can be fooled by a patient holding it in the mouth to show compliance and then removing the pill without ingestion of the study medication. Therefore, a more definitive approach to measure compliance is through measurement of study drug or an ingestible biomarker that can definitively ensure that the patient ingested the study medication.

Several markers, such as riboflavin, quinine, and acetazolamide, have been investigated as markers to indicate adherence of a subject to the proscribed drug schedule, but all are unsuitable for use for long-term monitoring. (Ramanujam, V. M., et al. Riboflavin as an oral tracer for monitoring compliance in clinical research. Open Biomark J 2011, 1-7 (2011); Babalonis, S., et al. Quinine as a potential tracer for medication adherence: A pharmacokinetic and pharmacodynamic assessment of quinine alone and in combination with oxycodone in humans. J Clin Pharmacol 55, 1332-1343 (2015); and Hampson, A. J., et al. A Pharmacokinetic Study Examining Acetazolamide as a Novel Adherence Marker for Clinical Trials. J Clin Psychopharmacol 36, 324-332 (2016)). These markers have short detection windows that restricts the adherence measurement to as short a period as 24 hours in the case of riboflavin. These markers fail to detect "white coat compliance subjects" where the subjects are non-compliant until shortly before the clinic visit and return to non-compliant behavior following the clinic visit. Because riboflavin and quinine may be introduced through the subject's diet, they are unreliable indicators of adherence. Acetazolamide also has several negative side affects, such as drowsiness, tingling, loss of taste, confusion, and tiredness at therapeutic doses. As a result, these markers are unsuitable for long-term monitoring.

It would therefore constitute a major advance in the art to provide biomarker compositions and techniques that enable long-term retrospective determinations of dosing, dosage, and administration schedule compliance of active agents, e.g., for time periods on the order of 7-10 days and even longer.

SUMMARY

Provided herein are methods and dose packs for the monitoring of medication adherence. One aspect of the technology is a dose pack for monitoring adherence of a subject to a dosing schedule. The dose packs may comprise a multiplicity of doses of an agent and a multiplicity of doses of a marker and be configured to isolate a pair of at least one of the multiplicity of doses of the agent and at least one of the multiplicity of doses of the marker for co-administration of the pair to the subject according to the dosing schedule. The pair may be included in a unitary dosage form or may be in paired or binary dosage forms. The agent may comprise a member selected from the group consisting of an active pharmaceutical ingredient, an investigational new drug, a drug candidate, an active substance, a combination of any of the foregoing, or a placebo. The dose pack may comprise a marking corresponding to the administration time according to the dosing schedule.

The multiplicity of doses of the marker may comprise at least two doses of two different markers. In some embodiments, the multiplicity of doses of the marker comprises at least three doses of three different markers. In particular embodiments, the multiplicity of doses of the marker comprises at least seven doses of seven different markers.

Any of the markers may be independently selected from the group consisting of active pharmaceutical compounds, over-the-counter (OTC) medications, generally-regarded-as-safe (GRAS) compounds, dietary supplements, food dyes, and combinations thereof. Any of the markers or a degradation product thereof may be capable of being detected in a sample obtained from the subject at least 72 hours following administration of the marker to the subject. In some embodiments, at least one of the markers is a histamine receptor ligand compound. In certain embodiments, at least one of markers is ranitidine, nizatidine, or famotidine. In particular embodiments, combinations of any two or all three of ranitidine, nizatidine, or famotidine are used.

In embodiments where the multiplicity of doses of the marker comprises at least two doses of two different markers, the pair may comprise at least two pairs of an agent and the two different markers. In some embodiments, the pair may comprise a first pair comprising at least one dose of the first marker, a second pair comprising at least one dose of the second marker, and a third pair comprising at least one dose of the third marker. In some embodiments, the pair is a unitary formulation comprising the dose of the agent and the dose of the marker. In other embodiments, the pair is a binary formulation comprising a first formulation comprising the dose of the agent and a second formulation of the dose of the marker.

Another aspect of the technology is a method for monitoring adherence of a subject to a dosing schedule. The method comprises obtaining a sample from the subject subsequent to the conclusion of a monitoring window and analyzing the sample for the presence or absence of a marker or a degradation product thereof. The method may further comprise providing the subject with a dose pack and/or providing the subject with the dosing schedule. The dose pack may be configured to isolate a pair of at least one of the multiplicity of doses of the agent and at least one of the multiplicity of doses of the marker for co-administration of the pair to the subject according to the dosing schedule during the monitoring window. The dose pack may comprise any of the dose packs described above. The dosing schedule may comprise a multiplicity of administration times for the administration of the pair to the subject according to the dosing schedule during the monitoring window.

In some embodiments, the monitoring window comprises at least two monitoring sub-windows comprising a multiplicity of administration times for different pairs comprising different markers during each of the sub-windows, respectively. In certain embodiments, the monitoring window comprises at least a first sub-window, a second sub-window, and a third sub-window comprising a number of administration times for a first pair, a second pair, and a third pair, respectively. In particular embodiments, the monitoring window comprises at least seven sub-windows.

The monitoring window may be at least three days. In some embodiments, the monitoring window may be at least seven days.

The method may further comprise repeating the obtaining the sample step and analyzing the sample step for one or more additional monitoring windows.

BRIEF DESCRIPTION OF THE DRAWINGS

FIG. 6A illustrates an exemplary representation table of a 7-day monitoring window with seven different marker-agent pairs administered during seven monitoring sub-windows, respectively, with subject compliance.

FIG. 6B illustrates an exemplary representation table of a 7-day monitoring window with seven different marker-agent pairs administered during seven monitoring sub-windows, respectively, with subject non-adherence (lack of taking the Day 2 dose and overdosing on day 6).

FIG. 7 illustrates time-course detection of the presence of three different histamine receptor ligand markers and various degradation products over a 10-day monitoring window.

DETAILED DESCRIPTION

Figure 1:
FIG. 1 illustrates a schematic representation of a dose pack.

The present disclosure relates generally to methods and dose packs for monitoring medication adherence. More specifically the present disclosure relates to methods of using markers, including histamine receptor ligands, and dose packs comprising the same for co-administration with agents to monitor adherence to a dosing schedule. The present disclosure provides several advantages, including monitoring over a full monitoring window and segmented monitoring to identify compliance over the full monitoring window.

As used in the specification and appended claims hereof, the singular forms "a", "an", and "the" include plural reference unless the context clearly dictates otherwise, and the terms "includes", "having", "has", "with", or variants thereof are intended to be inclusive in a manner similar to the term "comprising."

The disclosure, as variously set out herein in respect of features, aspects and embodiments thereof, may in particular implementations be constituted as comprising, consisting, or consisting essentially of, some or all of such variously described features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

Further, the disclosure contemplates restrictively defined compositions, methods, and products, e.g., wherein the invention as hereinafter claimed may be further specified in further proceedings by provisos or limitations excluding specific components, elements, operations, actions, ingredients, groups, moieties, parts, and/or structures, in relation to various disclosures, specifications, and exemplifications thereof set forth herein. Thus, for example, the disclosure contemplates restrictively defined compositions, e.g., a composition wherein specific active agent(s) and/or biomarker(s) described herein is/are not present in the composition as subsequently claimed.

Definitions

"Marker" (sometimes referred to as "biomarker") as used herein means any individual compound or combination of compounds that are capable of being detected in a biological sample following administration of the compound to a subject or any residue, metabolite, degradation product, or other detectable species derived from or associated with the compound (collectively referred to as "degradation product") capable of being detected in a biological sample following administration of the marker. Markers may include GRAS compounds, dietary supplements, OTC compounds, active pharmaceutical ingredients, including histamine receptor ligands, food dyes, or any combination of compounds thereof whether the compounds are in the same or different classes.

A dose of the marker may be administered in any suitable biomarkingly effective amount and formulation for administration for detection of the marker or degradation product in the sample according to the dosing schedule. The amount of the marker in a dose may be at lower than recommended doses, at recommended doses, or higher than recommended doses. In particular cases the biomarkingly effective amount is at least 1 mg and not more than 50 mg per dose or any biomarkingly effective amount or range between those limits. In particular cases the biomarkingly effective amount is at least 4 mg and not more than 30 mg or at least 4 mg and not more than 15 mg.

"Histamine receptor ligand" as used herein means any ligand capable of binding to any of the histamine receptors capable of binding histamine, including any of the $H_1$, $H_2$, $H_3$, or $H_4$ histamine receptors. The histamine receptor ligand may be an agonist, partial agonist, antagonist, or inverse agonist of the histamine receptor.

"Generally-regarded-as-safe (GRAS)" as used herein means any substance intentionally added to food that is generally recognized, among qualified experts, as having been adequately shown to be safe under the conditions of its intended use.

"Dietary supplement" as used herein means any vitamin; mineral; herb or other botanical; amino acid; dietary substance for use by man to supplement the diet by increasing the total dietary intake; or a concentrate, metabolite, constituent, extract, or combination of the preceding substances "Over-the-counter (OTC)" as used herein means any active pharmaceutical ingredient lawfully sold without prescription.

"Active pharmaceutical ingredients" as used herein mean any compound that provides pharmacological activity or other direct effect in the diagnosis, cure, mitigation, treatment, or prevention of disease, or affects the structure or function of the body or a subject.

"Agent" as used herein means any active pharmaceutical ingredient, investigational new drug, drug candidate, active substance, combination of any of the foregoing (e.g., combination of active pharmaceutical ingredients or combination of active pharmaceutical ingredients and investigational new drugs), or placebo.

A dose of the agent may be administered in any therapeutically effective amount for an active pharmaceutical ingredient or active substance for desired pharmacological activity or other direct effect in the diagnosis, cure, mitigation, treatment, or prevention of disease, or affects the structure or function of the body or a subject or any investigational amount for an investigational new drug or drug candidate. The dose of the agent may be administered in any suitable formulation.

"Placebo" as used herein means a pharmacologically inert preparation, including preparations typically uses in controlled experimental testing of the efficacy of another substance.

"Marker-agent pair" (sometimes referred to as simply "pair") as used herein means any suitable combination of a dose of the marker and a dose of the agent. The pair may be a unitary formulation where the dose of the marker and the dose of the agent are combined in an inseparable formulation. In other embodiments, the pair may be a binary formulation where the dose of the marker and the dose of the agent are combined in separable formulations, which may or may not be substantially similar in their visual appearance.

"Dose pack" as used herein means a product for the containment of one or more marker-agent pairs and configured for the subject's compliance with the dosing schedule.

"Dosing schedule" as used herein means a predetermined schedule of administration times of the pair to the subject.

"Monitoring window" as used herein means the temporal duration between a first predetermined administration time for a pair to the subject according to the dosing schedule and the obtainment of a sample from the subject. The monitoring window may be characterized by a multiplicity of predetermined administrations between the first predetermined administration time and obtainment of the sample from the subject and the temporal duration may be inferred from the timing of the predetermined administration times and/or frequency of the administration times. All of the administration times of the dosing schedule or any portion thereof may occur during the monitoring window.

"Monitoring sub-window" as used herein means a portion of the temporal duration of the monitoring window. The monitoring window may be characterized by a multiplicity of predetermined administrations for a particular marker when a combination of markers are used and the temporal duration of the sub-window may be inferred from the timing of the predetermined administration times and/or frequency of the administration times.

"Administration" as used herein means any suitable modality for administering the marker-agent pair to the subject. Examples of modalities suitable for administering the marker-agent pair include oral administration, parenteral administration, transdermal administration, intranasal administration, intravaginal administration, buccal administration, subcutaneous administration, or injection administration.

"Sample" as used herein means any physiological sample obtainable from a subject. Examples of samples include urine, saliva, tears, sweat, blood, plasma, lymph fluid, mucous, or tissue.

"Subject" as used herein means any vertebrate animal, including human. In particular uses of the term, a subject may be a patient seeking or undergoing treatment or a participant in a clinical trial.

Dose Packs

One aspect of the invention is a dose pack for monitoring adherence of a subject to a dosing schedule. The dose pack comprises a multiplicity of doses of an agent and a multiplicity of doses of a marker. The dose pack should be configured to isolate a marker-agent pair of at least one of the multiplicity of doses of the agent and at least one of the multiplicity of doses of the marker for administration of the pair to the subject according to the dosing schedule.

The marker may be any suitable marker that itself is capable of being detected in a sample obtained from the subject at least 72 hours (i.e., 3 days) following administration of the marker to the subject or a degradation product of the marker is capable of being detected over the same time period. In other embodiments, the marker or the degradation product thereof may be detectable in the sample for at least 4 days, 5 days, 6 days, 7 days, 8 days, 9 days, 10 days, 11 days, 12 days, 13 days, or 14 days.

A dose of the marker may be administered in any suitable biomarkingly effective amount and formulation for administration for detection of the marker or degradation product in the sample according to the dosing schedule.

The marker may be an active pharmaceutical compounds, over-the-counter (OTC) medications, generally-regarded-as-safe (GRAS) compounds, dietary supplements, food dyes, and combinations thereof. In some embodiments, the marker comprises a histamine receptor ligand compound. The histamine receptor ligand may comprise an $H_1$, $H_2$, $H_3$, or $H_2$ receptor ligand compound. The histamine receptor ligand compound may be an agonist, partial agonist, antagonist, and inverse agonist of the histamine receptor. The Examples below demonstrate the effective use of several histamine receptor ligands, ranitidine, nizatidine, famotidine, and combinations thereof, as markers. Moreover the Examples below demonstrate the effective use of combinations of active pharmaceutical compounds, OTC, GRAS compounds, and dietary supplements, specifically the combination of ranitidine, loperamide, dextromethorphan, famotidine, diphenhydramine, ascorbic acid, and riboflavin.

Preferred adherence markers should be persistent and detected in 100 percent of subjects 100 percent of the time, preventing the possibility of falsely indicating nonadherence when a subject actually ingested the marker. Conversely, an adherence marker should not be found in normal dietary sources or products frequently used by subjects to prevent the possibility of falsely indicating adherence when the marker is not actually ingested. "Accidental" exposure to the marker from pharmaceutical, OTC, or dietary supplement compounds should be minimal or able to be managed by having subjects avoid certain products. Since adherence is likely to be measured in studies of investigational new drugs, a marker should be free from physical and psychological effects that could be falsely attributed to the investigational drug. Additionally, the safety and toxicity data of a marker should be well known so that abnormal values in hematology, serum electrolytes and other laboratory studies do not confound the safety and toxicity data of the investigational new drug. Preferably, the marker should have data for long term exposure (e.g., up to a year) in a large number of patients from multiple classifications (e.g, adults and children or men and women) over many years. A marker should be free from medication-medication side effects which could either raise the level of the investigational new drug or the level of the marker leading to adverse events or falsely confirming adherence. Given the risk of pregnancy, an ideal marker should be pregnancy category A or B. The reasons noted above probably explain why despite their availability and great need for an adherence biomarker, the currently available adherence biomarkers (riboflavin, quinidine, acetazolamide) have not been widely used.

The $H_2$ ligands ranitidine, famotidine, diphenhydramine, and nizatidine possess many of the desired properties described above. The $H_2$ ligands are persistent in urine much longer than current markers, are not found in the normal diet, are safe and studied enough for OTC use, have a favorable side effect profile with few adverse effects, have been studied up to one year in clinical trials, are free from major medication-medication side effects, approved for pediatric use, and designated pregnancy category B. Compared to other ways of measuring adherence, urinary or salivary biomarkers are cheap, noninvasive, easy to use and have a very low potential to influence the placebo or dropout rate of a clinical study.

In some embodiments, the multiplicity of doses of the marker comprises at least two different markers. In particular embodiments, the multiplicity of doses of the marker comprise at least 3 different markers, 4 different markers, 5 different markers, 6 different markers, or 7 different markers.

In particular embodiments, the multiplicity of doses of the marker comprise as least one dose of a first marker, at least one dose of a second marker, and at least one dose of a third marker, wherein each of the first marker, the second marker, and the third marker are different markers. As a result, the pair comprises a first pair comprising at least one dose of the first marker, a second pair comprising at least one dose of the second marker, and a third pair comprising at least one dose of the third marker. Each of the first marker, the second marker, and the third marker are independently selected from the group consisting of active pharmaceutical compounds, over-the-counter (OTC) medications, generally-regarded-as-safe (GRAS) compounds, dietary supplements, food dyes, and combinations thereof.

The agent of the dose pack may be any active pharmaceutical ingredient, investigational new drug, drug candidate, active substance, combination of any of the foregoing (e.g., combination of active pharmaceutical ingredients or combination of active pharmaceutical ingredients and investigational new drugs), or placebo. A dose of the agent may be administered in any therapeutically effective amount for a active pharmaceutical ingredient or active substance for desired pharmacological activity or other direct effect in the diagnosis, cure, mitigation, treatment, or prevention of disease, or affects the structure or function of the body or a subject or any investigational amount for an investigational new drug or drug candidate. The dose of the agent may be administered in any suitable formulation.

The marker-agent pair may be combination of a dose of the marker and a dose of the agent. The pair may be a unitary formulation where the dose of the marker and the dose of the agent are combined in an inseparable formulation. In other embodiments, the pair may be a binary formulation where the dose of the marker and the dose of the agent are combined in separable formulations, which may or may not be substantially similar in their visual appearance.

The dose pack may include any suitable container for the marker-agent pair. In some embodiments, the dose pack comprises a blister pack configured to isolate the pair. The blister pack may be configured to isolate a unitary formulation. Alternative, the blister pack may be configured to isolate a binary formulation either in a single chamber or separate chambers.

The dose packs may comprise one or more markings corresponding to a co-administration time according to a dosing schedule to promote the subjects' compliance with the dosing schedule. The markings may be letters, numbers, colors, symbols, words, codes, e.g., machine-readable bar codes, or any other suitable marking to promote compliance.

FIG. 1 is a schematic representation of a dose pack in accordance with one aspect of the present disclosure. The dose pack may be packaged in a blister-pack or other suitable packaging configured to allow the subject to be in compliance with the dosing schedule. As shown, the active agent A is provided in 7 identical dose forms, namely, the oval-shaped tablets provided in the package. Positioned in close physical proximity to the respective dose forms of active agent A in the package are dose forms (tablets) B1-B7 of markers, wherein each of the tablets B1-B7 contains a different marker from all others. The package also is provided with markings, that may provide instructions or indicia that identify the co-administered dose forms of the active agent and the biomarker, for each of the 7 days of the dosing schedule, as "DAY ONE—A+B1" for the first day of the 7 day dosing schedule, "DAY TWO—A+B2" for the second day of the 7 day dosing schedule, "DAY THREE—A+B3" for the third day of the 7 day dosing schedule, etc., through as "DAY SEVEN—A+B7" for the final day of the 7 day dosing schedule.

The dosing composition in FIG. 1 may alternatively be presented in a color-coded format, in which each of the co-administered active agent and biomarker dose forms for a given day of the 7 day dosing schedule is of a same color, which is different from the colors of the dose forms for all other days of the 7 day dosing schedule. By way of example, the "DAY ONE" dose forms of A and B1 may each be tablets of red color, the "DAY TWO" dose forms of A and B2 may each be tablets of orange color, the "DAY THREE" dose forms of A and B3 may each be tablets of yellow color, the "DAY FOUR" dose forms of A and B4 may each be tablets of green color, the "DAY FIVE" dose forms of A and B5 may each be tablets of blue color, the "DAY SIX" dose forms of A and B6 may each be tablets of brown color, and the "DAY SEVEN" dose forms of A and B7 may each be tablets of black color.

As indicated, the active agent and biomarker may be combined in a unitary formulation, and the successive individual dose forms in such type of packaging may likewise be color-coded or otherwise be distinguished for separate administration in the dosing schedule.

It will therefore be appreciated that the active agent and biomarker materials may be constituted, formulated, and arranged in any suitable manner consistent with the present disclosure, to provide the active agent in a dosing format enabling the administration adherence of an individual, or group of individuals in a treatment or clinical population, to be readily assessed by appropriate detection and analysis modalities and equipment and/or materials.

Methods of Monitoring a Subject's Adherence to a Dosing Schedule

Another aspect of the invention is a method for monitoring a subject's adherence to a dosing schedule by detecting the presence or absence of a marker or of a degradation product thereof. At the conclusion of a monitoring window a sample is to be obtained from the subject and analyzed. When the marker or degradation product is detected, adherence to the dosing schedule may be determined. The presence of the marker in the sample indicates that the subject was adherent. Absence of the marker in the sample is indicative of lack of adherence of the subject to the dosing schedule.

The methods of monitoring may be facilitated by use of the dose packs described above. The dose packs configured to isolate marker-agent pairs allows for administration of the pair to the subject according to the dosing schedule during the monitoring window. Because the methods disclosed herein contemplate the use of different markers within the same monitoring window, one is able to determine compliance over the entirety of the monitoring window.

Figures 2A, 2B:
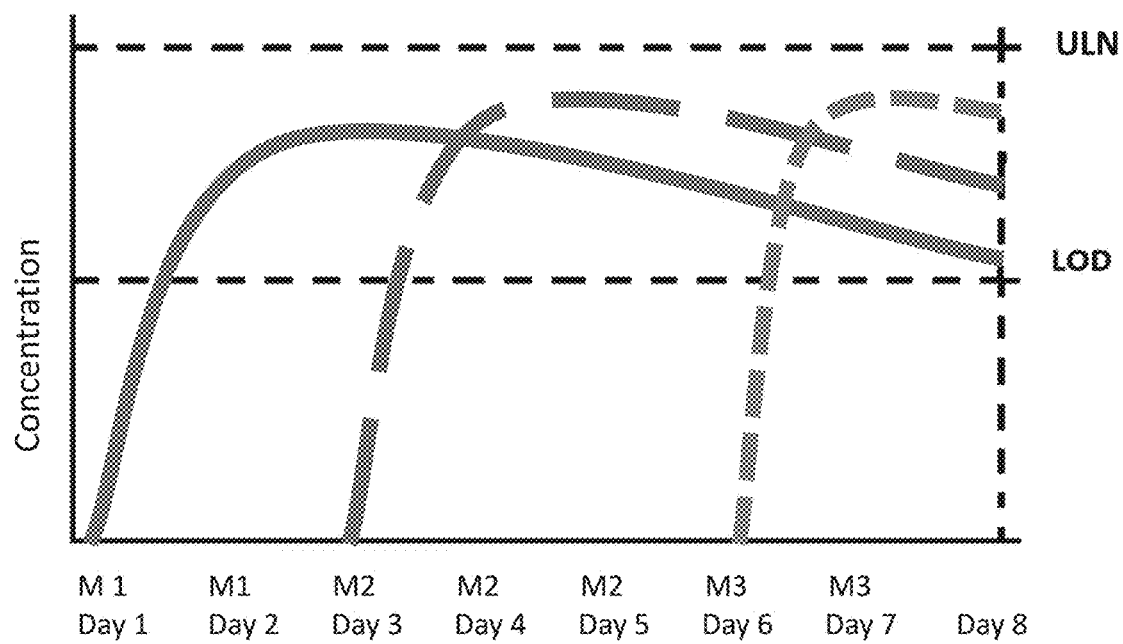
FIG. 2A illustrates an exemplary representation table of a 7-day monitoring window with three different marker-agent pairs administered during three monitoring sub-windows, respectively, with subject compliance.
FIG. 2B illustrates an exemplary time-course representation of a 7-day monitoring window with three different marker-agent pairs administered during three monitoring sub-windows, respectively, with subject compliance and corresponding with the table of FIG. 2A. (Solid line, concentration of $M_1$ in the sample; long dash line, concentration of $M_2$ in the sample; and short dash line, concentration of $M_3$ in the sample)

An exemplary illustration of the method and advantages of the present methods are presented in FIGS. 2A and 2B. FIG. 2A (topmost row 101) illustrates a 7 day monitoring window where the marker-agent pair is administered once a day for 7 days. The administration schedule for three particular marker-agent pairs are present in the second row 102 representing three monitoring sub-windows. Over the first two administration times, a first marker-agent pair comprising a dose of marker M1 is to be administered. Over the third, fourth, and fifth administration times, a second marker-agent pair comprising a dose of marker M2 is to be administered. Over the final two administration times, a third marker-agent pair comprising a dose of marker M3 is to be administered. The leftmost column 104 indicates the presence or absence of a particular marker (identified in the left-most column 103) detected in a sample collected from the subject.

FIG. 2B illustrates a time-course representation assuming compliance with the dosing schedule. With the administration of the market-agent pair at the first administration time (i.e., day 1) a detectable concentration of the marker $M_1$ or a degradation product thereof is detectable in a sample. Beginning with the third administration time, a detectable concentration of the marker $M_2$ or a degradation product thereof is detectable in a sample. Beginning with the sixth administration time, a detectable concentration of the marker $M_3$ or a degradation product thereof is detectable in a sample. With appropriate selection of the markers, when the sample is collected at the conclusion of the monitoring window on Day 8, detection of the presence of all of the markers above the limit of detection ("LOD") may be accomplished and compliance over the early sub-window, middle sub-window, and late sub-window of the eight day monitoring window may be determined.

In embodiments where quantification of the amount of marker or degradation product is desirable, adherence may be determined when the marker or degradation product is detected at a concentration within a tolerance range. In some instances, the lower end of the range will be the limit of detection specific to an analytical method or other lower limit line ("LLN") and the upper end of the range will be a upper limit line ("ULN"). When the marker or degradation product is determined to be within the predetermined tolerance, the presence of the marker within the tolerance may be noted in the right-most column 104 with a Y and determination of compliance may be indicated for a particular marker (left-most column 103) for the appropriate sub-window 105 indicated with an X.

Figure 3:
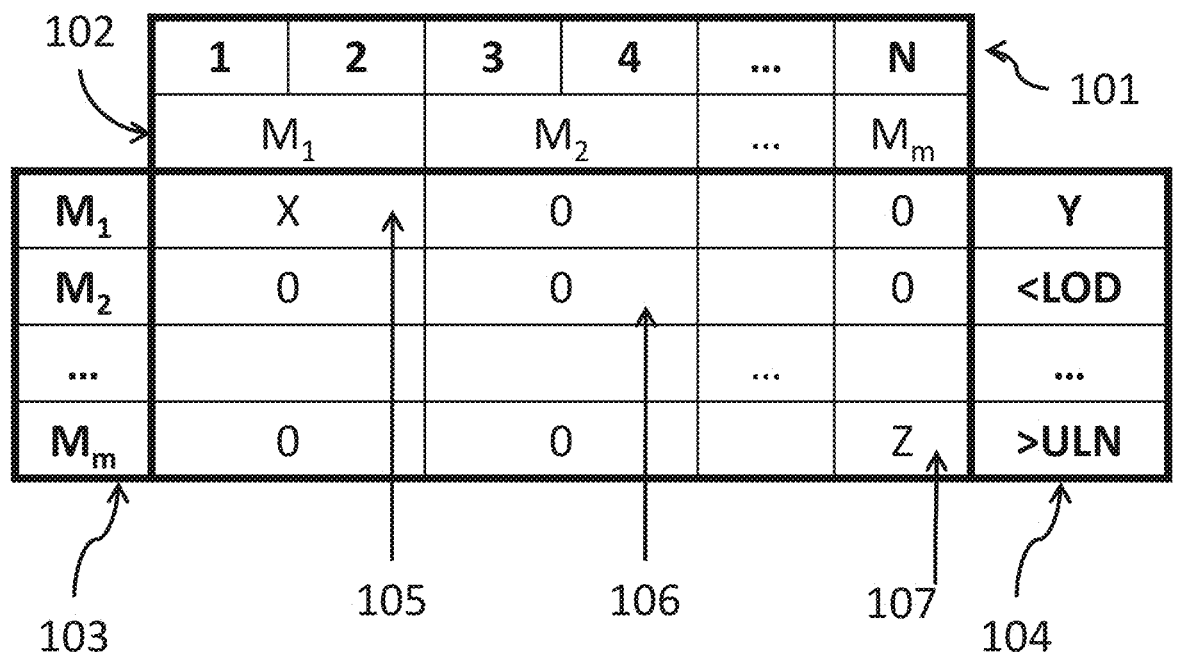
FIG. 3 illustrates a generalized representation table of a monitoring window with different marker-agent pairs administered during the monitoring sub-windows, respectively.

The methods exemplified above may be generalized. FIG. 3 shows a generalized representation table for N administration times. N may be any counting number appropriate for the duration of the monitoring window and frequency of administration times. In some embodiments, N may be greater than or equal to 1 and less than or equal to 90. In other embodiments, N may be greater than or equal to 3 and less than or equal to 14 or greater than or equal to 6 and less than or equal to 8.

There may be any appropriate number of distinct markers m, where m is a counting number greater than or equal to 1 and less than or equal to N. In particular embodiments, m may be 3, 4, 5, 6, 7, or more than 7. The Examples that follow demonstrate the use of 3 distinct markers and 7 distinct markers.

The generalized table may also include notations for markers detected below the LOD (noted as "<LOD" or "<" in right-most column 104). The corresponding monitoring sub-window 106 may be indicated by a null notation (in this case 0).

The generalized table may also include notations for markers detected above the ULN (noted as ">ULN" or ">" in right-most column 104). The corresponding monitoring sub-window 107 may be indicated by an overdose notation (in this case Z).

The monitoring window may have any number of monitoring sub-windows greater than or equal to 2 or less than or equal to N. In some embodiments, there are an equal number of sub-windows as distinct markers. In particular embodiments, there are at least 3 sub-windows, 4 sub-windows, 5 sub-windows, 6 sub-windows, or 7 sub-windows.

The sub-window may have any duration less than the monitoring window. The sub-window will include at least one administration time and any number of administration times for the desired duration. In some embodiments, the sub-window includes 1, 2, 3, 4, 5, or more than 5 administration times.

Figures 4A, 4B:
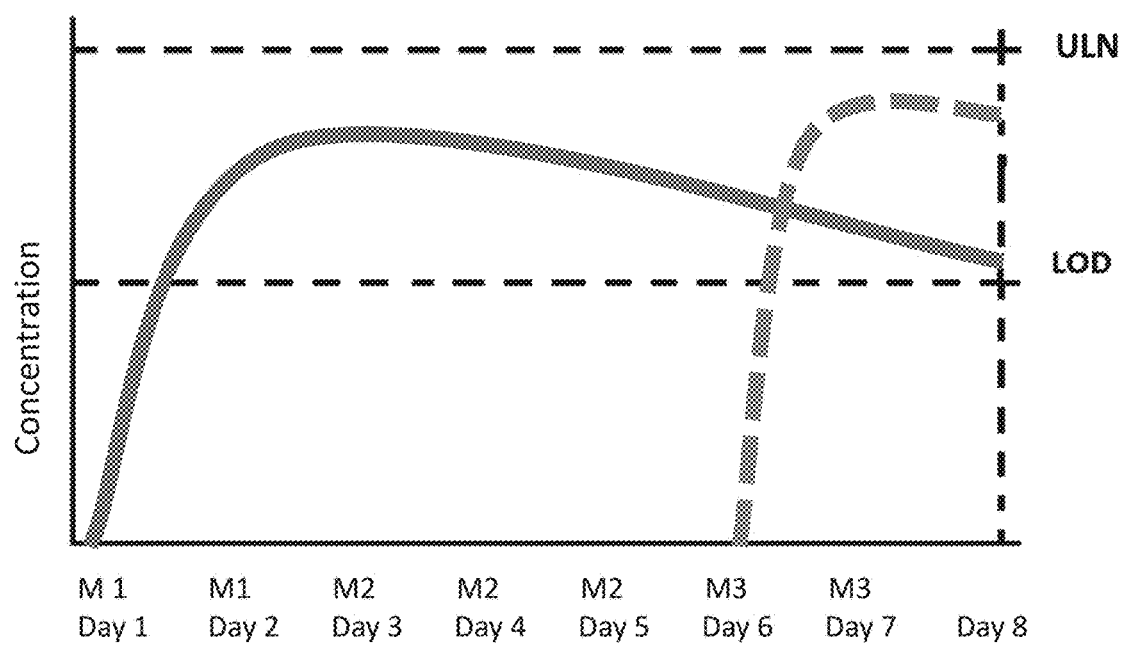
FIG. 4A illustrates an exemplary representation table of a 7-day monitoring window with three different marker-agent pairs administered during three monitoring sub-windows, respectively, with subject non-adherence.
FIG. 4B illustrates an exemplary time-course representation of a 7-day monitoring window with three different marker-agent pairs administered during three monitoring sub-windows, respectively, with subject non-adherence and corresponding with the table of FIG. 4A. (Solid line, concentration of $M_1$ in the sample and short dash line, concentration of $M_3$ in the sample)
Figures 5A, 5B:
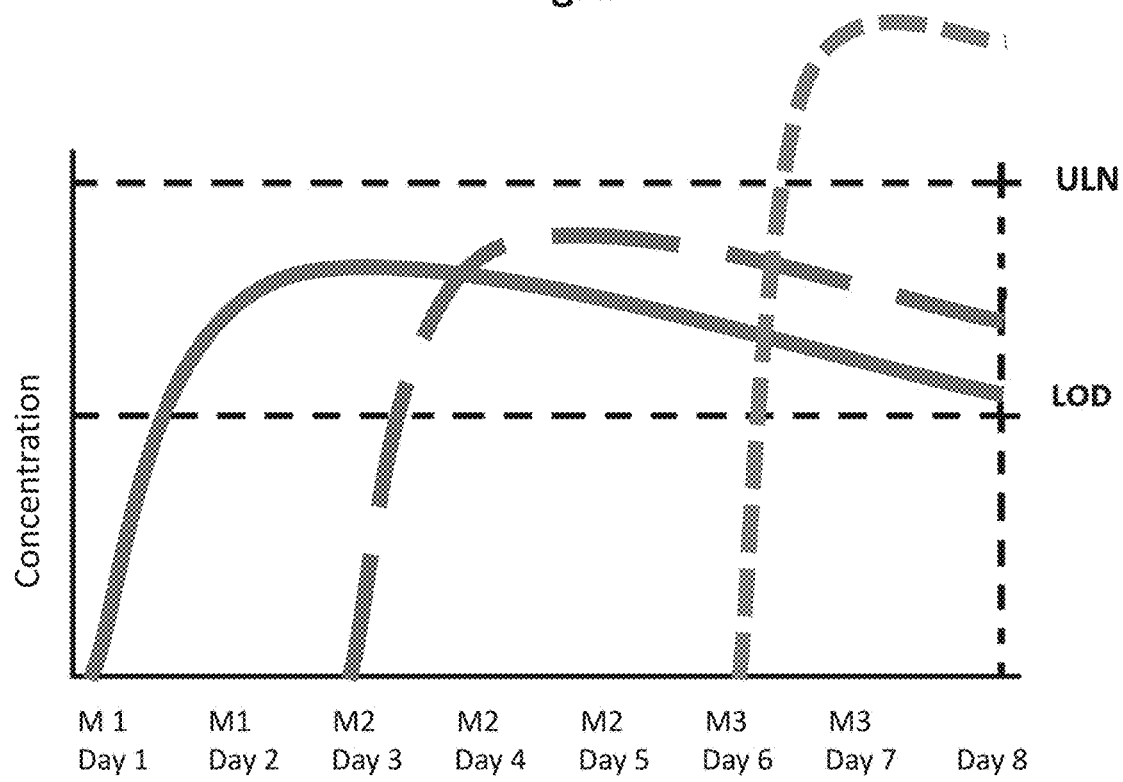
FIG. 5A illustrates an exemplary representation table of a 7-day monitoring window with three different marker-agent pairs administered during three monitoring sub-windows, respectively, with subject non-adherence.
FIG. 5B illustrates an exemplary time-course representation of a 7-day monitoring window with three different marker-agent pairs administered during three monitoring sub-windows, respectively, with subject non-adherence and corresponding with the table of FIG. 5A. (Solid line, concentration of $M_1$ in the sample; long dash line, concentration of $M_2$ in the sample; and short dash line, concentration of $M_3$ in the sample)

Employing this framework, additional exemplary illustrations are provided. FIGS. 4A and 4B illustrate the use of three distinct markers where marker $M_2$ is not detected. FIGS. 5A and 5B illustrate the use of three distinct markers where $M_3$ is detected above the ULN. FIG. 6A illustrates the use of seven distinct markers where each is detected within the desired tolerance. FIG. 6B illustrates the use of seven distinct markers were $M_2$ is detected below the LLN or LOD and $M_6$ is detected above the ULN.

The dose pack may have any appropriate multiplicity of marker-agent pairs. In some embodiments, the dose pack has the same number of pairs as the number of administration times for the monitoring window. If repeated monitoring is desired, the subject may be provided a new dose pack for the new monitoring window. In other embodiments, the dose pack has an integer multiple number of pairs as the number of administration times for the monitoring window, which may be used where monitoring of the subject is intended to be repeated.

In some embodiments, repeated monitoring may use two different agents during different monitoring windows. In particular embodiments, the earlier of different monitoring windows will use a placebo as the agent. Such monitoring may be useful for the identification of subjects capable of complying with a dosing schedule for selection for a clinical trial. In the later monitoring window, the same subject may be provided a multiplicity of marker-agent pairs where the agent is an active pharmaceutical ingredient, investigational new drug, drug candidate, active substance, or combination of any of the foregoing.

Uses of the Methods, Markers, and Dose Packs

The methods and dose packs of the present disclosure thus may be used in multiphasic courses of treatment, research studies, and clinical trials, in which early, middle, and late phase adherence can be easily determined by the methods and compositions described herein.

The disclosure in one aspect relates to a method of determining adherence to a predetermined dosing schedule of one or more administered composition, wherein the predetermined dosing schedule comprises a multiplicity of administered dosages, the method comprising co-administering with each of the administered dosages a biomarker, wherein the co-administered biomarker is different in at least two dosage administrations in the predetermined dosing schedule.

The biomarkers, as indicated, may be of any suitable type, and the different co-administered biomarkers in the at least two dosage administrations in the predetermined dosing schedule may comprise different biomarkers selected from the group consisting of GRAS compounds, dietary supplements, OTC compounds, dietary supplements, active pharmaceutical ingredients, including histamine receptor ligands, food dyes, or any combination of compounds thereof whether the compounds are in the same or different classes. Examples of markers include, but are not limited to, ranitidine, nizatidine, famotidine, cimetidine, loperamide, dextromethorphan, diphenhydramine, loratadine, chlorpheniramine, quinine, acetazolamides, ascorbic acid, riboflavin, L-cysteine, sodium benzoate, and licorice root extract. Markers may fall within more than one class depending on context. The Examples that follow show the use of ranitidine, nizatidine, famotidine, cimetidine, diphenhydramine, loperamide, dextromethorphan, ascorbic acid, and riboflavin. Those of skill in the art will appreciate that other markers whether alone or in combination may also be used.

Further, although the examples have been directed to quantitative detection of $H_2$ ligand compounds at a time or times subsequent to completion of a dosing schedule, it will be recognized that the biomarkers may comprise metabolites, degradation residues, bio-assimilation products, or other detectable species that derive from the administered $H_2$ ligand compounds, in addition to, or alternative to, such compounds themselves. As an illustrative example of metabolites for the aforementioned ligand receptor compounds, ranitidine produces the metabolites N-oxide ranitidine, S-oxide ranitidine, and desmethylranitidine, nizatidine produces the metabolites N-oxide nizatidine, S-oxide nizatadine and N2-monodes-methyl nizatidine, and famotidine produces the metabolite S-oxide famotidine. It will be appreciated that specific metabolites for monitoring purposes desirably have suitably long persistence in the physiological sample medium, e.g., a long half-life in plasma, blood, urine or other sample medium, for the verification monitoring of compliance or adherence to a desired or otherwise predetermined dosing schedule.

The method broadly described above may include the different co-administered biomarkers in the at least two dosage administrations in the predetermined dosing schedule comprising at least one histamine receptor ligand compound, e.g., in which the at least one histamine receptor ligand compound is selected from the group consisting of ranitidine, nizatidine, and famotidine. In specific embodiments, the method may include the different co-administered biomarkers in the at least two dosage administrations in the predetermined dosing schedule comprising at least two different histamine receptor ligand compounds, e.g., as selected from the group consisting of ranitidine, nizatidine, and famotidine. In still other embodiments, the method may include the predetermined dosing schedule comprising at least three administered dosages. For example, the different co-administered biomarkers in the at least three dosage administrations in the predetermined dosing schedule may comprise at least three different histamine receptor ligand compounds, such as ranitidine, nizatidine, and famotidine.

The dosing schedule and temporal duration of the dosing schedule may be widely varied in the broad practice of the present disclosure. For example, the predetermined dosing schedule may comprise from 1 to 4 administered dosages per day. In various embodiments, the predetermined dosing schedule may be from 1 to 31 days in duration. In other embodiments, the predetermined dosing schedule may comprise one administered dosage per day for a period of from 3 to 21 days. In still other embodiments, the predetermined dosing schedule may comprise one administered dosage per day for a period of 7 days. The method may be carried out in specific implementations, in which from 2 to 10 different biomarkers are co-administered with respective different administered dosages in the predetermined dosing schedule.

The method may be carried out, in which the same administered composition is administered in each of the administered dosages in the predetermined dosing schedule. Alternatively, the method may be carried out, in which two or more different administered compositions are administered in the predetermined dosing schedule. Thus, the method may be carried out, in which the administered composition or agent is the same in each of the administered dosages, and in which the co-administered biomarker is different in each of the administered dosages in the predetermined dosing schedule.

The methods may further comprise obtaining at least one sample from a subject to whom the administered composition has been co-administered with the biomarker in at least two administered dosages in the predetermined dosing schedule. The sample may be obtained from the subject contemporaneously with completion of the dosing schedule, e.g., within 5 days of completion of the dosing schedule, or alternatively within 3 days of completion of the dosing schedule, or within 2 days of completion of the dosing schedule, or within one day of completion of the dosing schedule. The at least one sample may include one or more samples obtained from the subject during the dosing schedule. In various embodiments, the at least one physiological sample can include samples obtained from the subject during the dosing schedule and contemporaneously with completion of the dosing schedule.

The methods may further comprise determining presence or absence of the biomarker or a metabolite, degradation residue, or bio-assimilation product of the biomarker, in the at least one sample. When the presence of the biomarker is determined, the amount or concentration of the biomarker may be determined. Such determinations may be made using any suitable methods, apparatus, assays, techniques, and the like. For example, the presence or absence of the biomarker, and/or concentration thereof, may be determined using liquid chromatographic processing of the sample. Alternatively, or additionally, presence or absence of the biomarker, and/or concentration thereof, may be determined using mass spectroscopy processing, ELISA or other antibody based detection or an alternative colorimetric or enzymatic form of detection of the marker or degradation product thereof in the sample.

The biomarker may be co-administered in any suitable manner in the methods. For example, the co-administered biomarker may be contained in at least one of the administered dosages in the dosing schedule, e.g., wherein the administered composition comprises a solid dose form of an agent. In such case, the biomarker may be contained in a coating on the solid dose form of the agent. Alternatively, the biomarker may be in a particulate form that is disposed in a capsule that also contains the agent. As a still further alternative, the biomarker may be in a layer of a tablet that comprises a further layer containing the agent.

The sample may be of any suitable type. The sample may comprise urine, saliva, tears, sweat, blood, plasma, lymph fluid, mucous, or tissue. The methods include obtaining specimens from the individual to whom the agent is being administered with biomarkers, wherein said specimens are processed for determination of biomarker presence and concentrations by a dedicated analytical test laboratory or other processing facility. For said purpose, the specimens may be collected with point of use care cups, stoppered vials, or other biological specimen containers in which the specimens may be transported, e.g., by mail or courier services, to test laboratory or other analysis locations.

The administered composition of agent and the biomarker may be co-administered by any suitable administration modality, such as a modality selected from the group consisting of oral, parenteral, transdermal, intranasal, intravaginal, buccal, subcutaneous, and injection. For example, the administered composition of agent and the biomarker may be co-administered by oral administration, in respective separate dose forms or alternatively in a unitary dose form comprising both the agent and the biomarker.

Samples may be taken at any suitable time or times in the dosing schedule or methods. In various embodiments, the sample may be taken at a time that is in a range of from 3 to 30 days, or 3 to 14 days, or 3 to 10 days, after the composition of agent and biomarker are co-administered. In other embodiments, the sample may be taken at least one day after the predetermined dosing schedule has been completed. Samples may be taken during as well as subsequent to completion of the dosing schedule, as may be appropriate in a given implementation of the methods.

The biomarker that is co-administered in each administered dosage in the predetermined dosing schedule may be administered in any suitable dosed amount. For example, the biomarker that is co-administered in each administered dosage in the predetermined dosing schedule may be in a biomarker dosage amount that is in a range of from 4 mg to 15 mg. The biomarker is appropriately present in the administered composition in each administered dosage in a biomarkingly effective amount, i.e., an amount that when properly administered to an individual is detectable in and quantitatively assessable from a physiological sample taken from the individual in an appropriate timeframe in relation to the performance of the dosing schedule.

The methods may be conducted, in which presence of the biomarker or metabolite(s) thereof, in a sample of a subject to whom the administered composition has been co-administered with the biomarker, above a specified cutoff level, is determined, as indicative that more than one dose of the administered composition has been taken, provides evidence of intentionally deceptive non-compliance by a clinical trial or research study participant with administration protocols of the trial or study, or intentionally deceptive or inadvertent non-compliance by a patient for whom the administered composition has been prescribed according to the dosing schedule. The methods may be conducted in a clinical trial of the administered composition, or in a research study of the administered composition, or in any other investigative or clinical effort in which administration compliance is required in order to achieve an appropriate or otherwise desired outcome. The methods may be useful for directly observed therapy protocols to ensure proper compliance with a dosing schedule.

In another aspect, a dosing composition, comprising a multiplicity of dose forms of one or more administrable composition, adapted to be administered in a dosing schedule is provided. In the dosing composition, the multiplicity of dose forms may have associated therewith different biomarkers for co-administration with the dose forms. In such dosing composition, the multiplicity of dose forms associated with respective different biomarkers may be packaged with each of the dose forms being disposed in the package in physical proximity to its associated biomarker and demarcated in the package for co-administration.

The dosing composition may be constituted such that each of the multiplicity of dose forms associated with different biomarkers for co-administration with the associated dose forms, comprises a dose form containing the associated biomarker. The dose forms may comprise solid dose forms of an agent. The dosing composition may be constituted such that each of the multiplicity of dose forms including an agent associated with different biomarkers for co-administration comprises the associated biomarker in a coating on the solid dose form of the agent. Each of the multiplicity of dose forms including an agent associated with different biomarkers for co-administration comprises the associated biomarker in a particulate form that is disposed in a capsule that also contains a particulate form of the agent. In still other embodiments, each of the multiplicity of dose forms including an agent associated with different biomarkers for co-administration comprises the associated biomarker in a layer of a tablet that comprises a further layer containing the agent. Accordingly, any suitable dose forms are contemplated, and in general each of the multiplicity of dose forms including an agent associated with respective different biomarkers for co-administration, may comprise a dose form adapted for administration by any suitable administration modality, e.g., an administration modality that is selected from the group consisting of oral, parenteral, transdermal, intranasal, intravaginal, buccal, subcutaneous, and injection. The dosing composition may be for oral administration and may comprise the biomarker in a biomarkingly effective amount. Such biomarkingly effective amount may be in a range of from 4 mg to 15 mg, or in other appropriate ranges, or amounts. The dosing composition may be constituted having a respectively different biomarker associated therewith.

In another aspect, the disclosure relates to a method of conducting a clinical trial or research study of a candidate active pharmaceutical ingredient, comprising administering the candidate active pharmaceutical ingredient to individuals of a patient population for the clinical trial or research study in accordance with a predetermined dosing schedule, wherein the candidate active pharmaceutical ingredient is provided to such individuals from a dosing composition of the present disclosure, as described herein. In such method, the physiological samples may be taken from the individuals and assessed for presence of biomarkers therein indicative of individual compliance with the dosing schedule. The method may further comprise discharging from the patient population any individuals whose physiological samples are determined to be noncompliant with the dosing schedule, or otherwise performing a responsive action to ensure accuracy and biostatistical reliability of the clinical trial or research study.

The present disclosure relates to histamine receptor ligands and metabolites that are usefully employed as biomarkers to permit longitudinal determinations of dosing, dosage, and medication schedule compliance to be made, for periods far longer than those enabled by currently used or proposed biomarkers. The biomarkers comprise histamine receptor ($H_1$, $H_2$, $H_3$, $H_4$) ligands (including histamine receptor agonists, partial agonists, antagonists, and inverse agonists) and their metabolites, which have been found, in contrast to previously proposed and available biomarkers, to provide effective biomarking efficacy for periods as long as 7-10 days and longer. Correspondingly, the present disclosure relates in various aspects to use of histamine receptor ($H_1$, $H_2$, $H_3$, $H_4$) ligands and their metabolites as markers to measure long-term adherence to medication regimens.

The use of histamine receptor ligands (agonists, partial agonists, antagonists, and inverse agonists) offers many advantages over the current methods of measuring medication adherence. These histamine receptor ligand compounds can be used as longitudinally persistent biomarkers that are combined along with other medications in both clinical and research settings to confirm ingestion of either prescribed or investigational medications. Many of these histamine receptor compounds when used as biomarkers can readily be found in urine and other physiological samples, do not interact appreciably with other medications, and have well-established pharmacological and safety profiles. Because many of these ligand compounds are used to treat commonly occurring disease states and physiological conditions, most individuals have been exposed to one or more doses of such compounds, at significantly greater concentrations in prior therapeutic use, thereby minimizing the risk of undesirable drug-drug interactions or incidence of significant side effects when used as ingestable biomarkers. Most importantly, when one or more biomarkers of the present disclosure are used together, they serve to confirm long-term (i.e., weekly to monthly) adherence, or alternatively non-adherence, to medication administration schedules, thereby achieving a fundamental advance in the art, in relation to currently deployed biomarkers, which as discussed herein are characteristically effective for periods on the order of 24-48 hours.

Detection of the biomarker ligand compounds also entails the advantage that they do not require venipuncture or other relatively complicated procedures for sample preparation for biomarker assaying in the methods provided, and urine, sweat, tears, may be employed without the necessity of invasive sampling of tissue or other biological media. Further, biomarker assaying can be readily accomplished using simple assay techniques, e.g., standard liquid chromatography and mass spectroscopy techniques. Data analysis associated with such biomarker assaying is also straightforward and does not involve the establishment of an individual's baseline levels, dietary restrictions, or normalization of an individual's physiological function. Accordingly, no additional effort on the part of the patient is required, and results can, for example, be obtained from urine samples collected as part of the standard protocols that are performed during the routine clinical and research visits of the patient. In this respect, it is to be noted that in clinical trials, the use of complicated digital technology may falsely elevate dropout rate of clinical study participants, not from any factors related to the study drug, but from the patient burden entailed in using complex technological devices. Accordingly, the use of the biomarker ligand compounds provides a further benefit in the simplicity and ease of obtaining samples.

In one aspect, the present disclosure relates to a method of determining adherence to a predetermined dosing schedule of an administered composition, said method comprising co-administering with the administered composition a biomarker comprising at least one histamine receptor ligand compound. In such method, the histamine receptor ligand compound may comprise an $H_2$ ligand compound. The biomarker in the administered composition is advantageously present in a biomarkingly effective amount. The administered composition may be of any suitable type, and may for example comprise an active pharmaceutical ingredient, such as an investigational new drug. In specific embodiments, the biomarker may comprise one or more of ranitidine, nizatidine, and famotidine. The dosing schedule may comprise temporal portions in each of which the administered composition contains a different biomarker. For example, there may be two or three, or more, temporal portions of the dosing schedule. The dosing schedule may be of any suitable duration, e.g., one week in duration. The histamine receptor ligand compound that is co-administered with the administered composition may be of any suitable type, and may for example comprise a compound selected from the group consisting of agonists, partial agonists, antagonists, and inverse agonists of the histamine receptor. The method may be conducted in a clinical trial of the administered composition, or alternatively in a research study of the administered composition, or in other administered composition application, according to any suitable protocols, restrictions, objectives, and/or requirements.

The method may further comprise obtaining a sample from a subject to whom the administered composition has been administered with the biomarker, and may further comprise determining presence or absence of the biomarker or a metabolite, degradation residue, or bio-assimilation product of the biomarker, in the sample. When presence of the biomarker is determined, an amount or concentration of the biomarker may also be determined, so that the determination comprises a quantitation of the biomarker. Any suitable methodology or technique may be used in determinations related to the biomarker. For example, presence or absence of the biomarker may be determined by liquid chromatographic processing of the sample, or by mass spectroscopy processing of the sample, or in other suitable manner.

Likewise, the co-administering in the method may comprise contemporaneous administration of the administered composition and administration of the biomarker. As noted above, the agent and biomarker in the administered composition may be in a unitary composition. For example, the administered composition may comprise a solid dose form of an agent with the biomarker contained in a coating on the solid dose form of the agent, or wherein the biomarker is in a particulate form that is disposed in a capsule that also contains the agent, or wherein the biomarker is in a layer of a tablet that comprises a further layer containing the agent.

The sample and administration means used in the methods may be any of those noted above and available to those skilled in the art. Urine is a particularly advantageous physiological sample, due to its use as a conventional sample medium in physical examinations, clinical trials, research studies, etc. Oral administration is also particularly useful due to ease of administration. The sample may be taken at any suitable time in relation to the dosing schedule. For example, the sample may be taken at a time that is in a range of from three days to 30 days after the administered composition and biomarker are co-administered. In other embodiments, the sample may be taken at a time that is in a range of from three days to 14 days after the administered composition and biomarker are co-administered. In still other embodiments, the sample may be taken at a time that is in a range of from three days to 10 days after the administered composition and biomarker are co-administered. In various embodiments, the sample may be taken at least one day after a multi-day course of co-administration of the administered composition and biomarker.

The disclosure relates in another aspect to a method of determining adherence to a predetermined dosage schedule of an administered composition, wherein the predetermined dosing schedule comprises a multi-day dosage schedule, the method comprising co-administering with the administered composition in each dosage administration in the multi-day dosage schedule a biomarker comprising at least one histamine receptor ligand compound, wherein the co-administered biomarker is different in at least two dosage administrations in the multi-day dosage schedule.

The above method may be carried out in any suitable manner. For example, the co-administered biomarker may be different in at least three dosage administrations in the multi-day dosage schedule. The co-administered biomarker may be of any suitable type, and may for example be selected from the group consisting of ranitidine, nizatidine, and famotidine. A single biomarker may be used in multiple doses in the multi-day dosing schedule. For example, a first marker may be used in two or more doses in the beginning of the dosing schedule and then a second marker may be used in two or more doses in the middle of the dosing schedule. If needed further markers may be used in two or more doses at further time points in the dosing schedule. The foregoing method may further comprise obtaining a sample from a subject to whom the administered composition has been co-administered with the biomarker in at least two dosage administrations in the multi-day dosage schedule. In other embodiments, a sample may be obtained from the subject to whom the administered composition has been co-administered with the biomarker in at least three dosage administrations in the multi-day dosage schedule. The foregoing method may be carried out, as further comprising determining presence or absence of the biomarker or a metabolite, degradation residue, or bio-assimilation product of the biomarker, in the physiological sample. In various embodiments, when the presence of the biomarker is determined, an amount or concentration of the biomarker is concurrently determined. The method may be carried out with any suitable histamine receptor ligand compound. In various embodiments, the method is carried out with $H_2$ receptor ligand compounds. The biomarker in the foregoing method may be present in the administered composition in a biomarkingly effective amount.

The co-administering of the administered composition and the biomarker may comprise contemporaneous administration of the administered composition and administration of the biomarker, e.g., in simultaneous or sequential manner. The administered composition may contain the biomarker in a unitary composition as described above or in separate dosage forms. The sample may be taken at any suitable time in relation to the administration of the administered composition and biomarker. For example, the sample may be taken at a time that is in a range of from three days to 30 days, 3 to 14 days, 3 to 10 days, 3 to 7 days or at least one day, after the administered composition and biomarker are co-administered.

In another aspect, a pharmaceutical composition comprising an agent and an administration compliance biomarker is provided, the biomarker comprising at least one histamine receptor ligand compound. The histamine receptor ligand compound may in various embodiments comprise an $H_2$ receptor ligand compound, e.g., one or more of ranitidine, nizatidine, and famotidine.

A further aspect of the disclosure relates to a packaged pharmaceutical composition, comprising multiple, differing dose forms of the pharmaceutical composition demarcated for sequential administration, each of the dose forms containing a same agent, the dose forms including a first set of the dose forms containing a first biomarker comprising at least one histamine receptor ligand compound, and a second set of the dose forms containing a second biomarker comprising at least one histamine receptor ligand compound, wherein the histamine receptor ligand compound is the same in each dose form in the first set of the dose forms, the histamine receptor ligand compound is the same in each dose form in the second set of the dose forms, and the histamine receptor ligand compound in the first set of the dose forms is different from the histamine receptor ligand compound in the second set of the dose forms. These dose forms may further include a third set of the dose forms containing a third biomarker comprising at least one histamine receptor ligand compound, wherein the histamine receptor ligand compound is the same in each dose form in the third set of the dose forms, and histamine receptor ligand compound in the third set of the dose forms is different from the histamine receptor ligand compound in each of the first and second sets of the dose forms. The histamine receptor ligand compound in each of the sets of the dose forms may comprise an $H_2$ receptor ligand compound.

Although the examples show the use of 3 and 7 biomarker compounds, it will be appreciated that the utility of the present disclosure is not thus limited, and that any suitable number of biomarker compounds may be utilized, and that a specific one of multiple biomarkers may be utilized for a specific day or days in a multi-day administration of a composition including the biomarker. For such purpose, the biomarker may be co-administered with the agent, but in preferred practice, the biomarker is compounded or formulated in the composition to be administered. Such compositional presence of the biomarker or biomarkers (it being further appreciated that multiple biomarkers can be utilized with a specific composition, as an alternative to use of single biomarker with the specific composition) can be effected in any suitable manner.

For example, the biomarker(s) can be blended with an API in a suitable dose form for administration, at the time of production of the API dose form. Alternatively, the biomarker(s) can be associated with a pre-existing API dose form, in which biomarker-containing coatings are applied to the pre-existing API dose form, or in which biomarker-containing material is added in a particulate form to an API formulation in particulate form in a capsule, as an oral dose form. As a further variation, and API formulation may be tableted on a substrate or base layer of biomarker-containing material, to provide a multilayer tablet dose form comprising the API and the biomarker(s). In other embodiments, over-encapsulation of the API dose form may be carried out so that the overlying capsule containing the API dose form is appropriately loaded with a predetermined quantity of the biomarker, e.g., in a loose form within the outer capsule, exterior to the solid dose form that is disposed in the capsule. It will be appreciated that any of a wide variety of techniques may be employed to associate the biomarker with the API dose form, so that the biomarker and the API dose form can be co-administered simultaneously or contemporaneously.

It will be further appreciated that for purposes of administering a same API formulation with different biomarkers during specific phases of a multiphase administration regime, the API formulation dose form and associated biomarker can be packaged so that the API formulation/biomarker combination is identified for a specific phase of the multiphase administration regime. By way of specific example, the API formulation may comprise a solid dose form, such as a tablet or lozenge containing the API formulation, which is encased in a coating containing the biomarker, with the coatings containing the different biomarkers being of different colors, each associated with a specific phase of the multiphase administration schedule.

As a further elaboration of such example, the initial API dose form may be overcoated with a red shell coating containing a first biomarker, to be taken by the clinical trial or research study participant, or otherwise by a patient, during a first phase of the multiphase schedule, the intermediate API dose form may be overcoated with a green shell coating containing a second biomarker, to be administered during a middle phase of the multiphase schedule, and with a final API dose form being overcoated with a blue shell coating containing a third biomarker, to be administered during a final phase of the multiphase schedule. The respectively different colored API/biomarker dose forms therefore may be packaged in a blister pack, so that dose forms of a same color are segregated for access by an individual during the appropriate phase for which the dose form of such color are to be taken by the individual.

Further, although the preceding examples have been directed to quantitative detection of $H_2$ ligand compounds at a time or times subsequent to completion of a dosing schedule, it will be recognized that the biomarkers may comprise metabolites, degradation residues, bio-assimilation products, or other detectable species that derive from the administered $H_2$ ligand compounds, in addition to, or alternative to, such compounds themselves. As an illustrative example of metabolites for the aforementioned ligand receptor compounds, ranitidine produces the metabolites N-oxide ranitidine, S-oxide ranitidine, and desmethylranitidine, nizatidine produces the metabolites N-oxide nizatidine, S-oxide nizatadine and N2-monodes-methyl nizatidine, and famotidine produces the metabolite S-oxide famotidine. It will be appreciated that specific metabolites for monitoring purposes desirably have suitably long persistence in the physiological sample medium, e.g., a long half-life in plasma, blood, urine or other sample medium, for the verification monitoring of compliance or adherence to a desired or otherwise predetermined dosing schedule.

It will also be appreciated that the biomarkers of the present disclosure may comprise derivatives, analogs, and differing forms (salts, solvates, polymorphs, etc.) of existing $H_2$ receptor ligand compounds that are derivatized or otherwise structurally revised from their existing forms, to enhance their utility and biomarking effectiveness in the compositions and methods of the present disclosure. In various instances, the histamine receptor ligand compounds may produce metabolites that are higher in concentration than the peak concentration of the ligand compound itself and thus more readily detected as biomarker species subsequent to administration.

As indicated herein, the biological specimens/samples taken from individuals to determine adherence to the dosing schedule may be of any suitable type, such as body fluids, cellular or tissue samples, or any other biological material deriving from the individual that is able to be analyzed to determine whether the desired amount of the biomarker(s) indicative of adherence to the dosing schedule is present in the biological specimen. Although urine is described as an illustrative biological specimen material in the examples, it will be recognized that any other biological material amenable to determination of biomarkers may be employed, e.g., blood, tears, plasma, sweat, sputum, exhalation fluid, etc.

Thus, a combinatorial or multiplexed co-administration scheme may be employed to assess adherence to a dosing schedule in a precise manner, wherein the specific dose or doses not administered can be readily determined. Accordingly, the nature and extent of any non-compliance to the dosing schedule can be evaluated and remedial treatment or other action appropriate to the situation can be taken. For example, the remedial treatment may involve prolongation of the period of treatment, or alteration of the further treatment to include other or additional active agents or increases of the amount of administered active agent in the further treatment. As another example in the context of a clinical trial, the non-compliance to the dosing schedule can be evaluated as to the biostatistical impact of such non-compliance, and the individual participant of the clinical trial who was determined not to have adhered to the dosing schedule can be discharged from the clinical trial patient population, if and as appropriate.

Biomarkers usefully employed in the broad practice of the present disclosure may be of any suitable type, and derive from any suitable source. For example, biomarkers may be employed that are known medical and clinical character, and that are approved or otherwise acceptable with respect to any applicable regulatory requirements, such as pharmaceutical compounds with known safety and toxicity data, dietary supplements, food dyes, and compounds generally regarded as safe (so-called GRAS substances). Examples of potentially useful pharmaceutical compounds in specific applications of the present disclosure include histamine receptors ligands such as ranitidine and diphenhydramine, dietary supplement components such as riboflavin, GRAS compound such as ascorbic acid, and food dyes such as FD&C Blue 1.

As indicated, biomarkers may be associated with one or more active agents to be administered, in any suitable manner. For example, the biomarkers may be provided as separately constituted physical formulation dose forms for co-administration with the dose forms of the active ingredient, or the biomarkers may be contained in or incorporated with the active ingredient in any suitable manner. In addition, although the foregoing illustrative discussion has been directed to single ingredient biomarkers, it will be appreciated that a biomarker may be employed in accordance with the present disclosure, wherein the biomarker comprises multiple biomarker species in accommodation with one another in the biomarker, so that respective different ones of different biomarkers may comprise different formulations of biomarker species, such as formulations in which each biomarker species is different from all other biomarker species in other biomarkers, or alternatively, formulations in which proportions of constituent biomarker species are different in different biomarkers, or in which respective biomarkers are otherwise demarcated or distinguished, or demarcatable or distinguishable, from one another.

EXAMPLES

The following Examples illustrate the practice of the biomarker monitoring methodology of the present disclosure, utilizing histamine receptor ligand compounds and/or their metabolites, in accordance with the disclosure. The ensuing described examples utilize widely available over-the-counter (OTC) $H_2$ receptor antagonists, commonly referred to as $H_2$ blockers, including ranitidine (the active pharmaceutical ingredient in Zantac®), nizatidine (the active pharmaceutical ingredient in Axid®) and famotidine (the active pharmaceutical ingredient in Pepcid®), which are commonly administered at dosages of 40 mg to 150 mg of the active pharmaceutical ingredient (API), but which when used as biomarkers in accordance with the present disclosure are administered at dosages that are 10 times or more lower than such conventional therapeutic dosages. This reduction of dosages to small fractions of conventional therapeutic dosages further minimizes the risk and incidence of any adverse pharmacological activity, drug-drug interactions, and/or biomarker-mediated side effects.

The reduction of dosages to small fractions of conventional therapeutic dosages has the further benefit that it enables identification of patients who use OTC medications such as those identified above (e.g., Zantac®, Axid®, Pepcid® and the like) instead of the biomarker. This substantial difference in administered OTC medication dosages and biomarker dosages is of particular advantage in clinical trials and research studies, for the purpose of ensuring compliance with clinical trial or research study protocols and achieving integrity and reliability of results.

It will be apparent from the foregoing that the amounts of the respective biomarkers employed for monitoring of administered compositions can be varied to provide appropriate physiological sample persisting concentrations, depending on the specific biomarker and the sensitivity and detection limits of the apparatus used to quantitate the biomarker concentrations in the physiological samples that are monitored.

It will be further appreciated that the monitoring quantitation of the respective biomarkers can be utilized to determine overdosing events, in which the administered composition is taken in one or more doses beyond the prescribed or otherwise predetermined appropriate amount of the composition. The use of multiple biomarkers thus permits appropriate temporal specification of the overdosing event, as occurring at a specific time or time window in the preceding period for which monitoring is conducted (e.g., an early week overdose, midweek overdose, or late week overdose)

will be reflected by the corresponding biomarker "over-concentration" in the urine or other physiological sample of the individual subject.

Example 1: Three Marker Sequencing

We have completed a preliminary IRB-approved clinical study where ranitidine, nizatidine, and famotidine were administered to provide clinical samples for development of the assays to detect $H_2$ antagonists in the urine. Single and multiple doses of ranitidine, nizatidine and famotidine were studied in healthy volunteers and urinary concentrations of parent drug and metabolites were measured over time using HPLC with mass spectrometry detection. The data showed that very low doses (20 times lower than prescribed doses and 10 times lower than OTC doses) of ranitidine (15 mg per dose for 3 days), nizatidine (15 mg per dose for 3 days) and famotidine (4 mg per dose for 2 days) can be reliably detected in urine for at least 96 hours after administration with ranitidine persisting longer in urine than the other drugs (data not shown).

Notably, when study subjects were dosed with a sequential combination of ranitidine 15 mg per day given on days 1-3, nizatidine 15 mg/day given on days 4-6 and famotidine 4 mg/day given on days 7 and 8 were administered and urine collected daily for 9 days, each drug was detected in urine only on the day after administration and all three drugs were detectable in urine on days 7, 8 and 9 (FIG. 2). The results from this experiment demonstrated that the approach is feasible and that the methods for detecting each compound have sufficiently low detection limits to detect each drug during a single weekly visit to the clinic. In a clinical trial setting, compliance can be demonstrated depending on which of the 3 drugs are detectable at 7-8 days.

Example 2: Seven Marker Sequencing

In the Examples that follow, 7 different markers are dosed over a 7 day, one week, time period with each day of the week being assigned a different marker. Detection of all 7 markers at day 8 confirms 100% adherence over the previous week. Detection of a particular marker can also be tied to adherence on the day to which it was assigned. Conversely, the absence of a particular marker suggests nonadherence on the day to which it was assigned. The examples also show how sequencing the markers confirms adherence over time, the difference between suitable and unsuitable markers, and among the suitable markers, the advantages and disadvantages of each. Ultimately, the examples demonstrate the superiority of the histamine receptor ligands as markers both when used individually, when sequenced in combination together or when sequenced in combination with other markers.

Selection of Markers for Sequencing

Markers can be found from lists of dietary supplements, food additives, generally regarded as safe (GRAS) compounds, pharmaceutical compounds or be any compound that is excreted in blood, urine, saliva or other collectible fluid or tissue for which a method of detection already exists or can be developed. Previously studied and clinically used markers include riboflavin, quinine and acetazolamide. Riboflavin is a dietary supplement and food additive, quinine is a food additive in low doses and a pharmaceutical compound in higher doses, and acetazolamide is a pharmaceutical compound. In the experiment below, 7 markers were selected based on our prior unpublished experiments that suggested suitability as a marker species. Riboflavin was included as a known comparator for the other markers. Quinine and acetazolamide were not used given the safety concerns and adverse effects at pharmacologically active doses. The markers selected were Ranitidine 150 mg, Loperamide 2 mg, Dextromethorphan 30 mg, Famotidine 20 mg, Diphenhydramine 25 mg, Ascorbic Acid 1000 mg and Riboflavin 32 mg. Ranitidine, Loperamide, Dextromethorphan, Famotidine and Diphenhydramine are pharmaceutical compounds and were used at approved over the counter (OTC) doses. Ascorbic Acid is a dietary supplement, food additive and GRAS compound.

Example 2A: Seven Marker Sequencing with Adherence

Four subjects ingested the following markers over a 7 day period: ranitidine 150 mg day 1, loperamide 2 mg day 2, dextromethorphan 30 mg day 3, famotidine 20 mg day 4, diphenhydramine 25 mg day 5, ascorbic acid 1000 mg day 6, and riboflavin 32 mg day 7. Riboflavin was prepared by a compounding pharmacy. All other markers were obtained from commercial sources. Urine and saliva were collected prior to each day's dosing of marker confirming the presence or absence of markers before the experiment started. It also means that the marker dosed on day 1 (ranitidine) would not be detected in a subject's urine and saliva until day 2. The presence of all 7 markers at day 8 would confirm that all markers were ingested in the previous 7 day one week period.

Healthy volunteers with no recent exposure to the markers who were not currently taking prescribed medications, OTC medications or vitamins and supplements were chosen. Exposure to the markers more than one month before starting the experiment was allowed and no dietary restrictions were required. Subjects were given a 7 day blister pack with markers sequenced in the order above. Subjects verbally confirmed they understood the urine and saliva collection procedures. Instructions printed on the marker blister pack instructed subjects to collect urine and saliva each morning before they took the daily dose of marker. They were also instructed to take the daily dose of marker close to the same time each day.

Description of the Marker Species

Ranitidine and Famotidine are Histamine-2 ($H_2$) antagonists or $H_2$ blockers and have been used for over 20 years to treat peptic ulcer disease and symptoms of gastroesophageal reflux disease (GERD). Ranitidine is available OTC as Zantac and Famotidine is available OTC as Pepcid. Pharmacologically, $H_2$ antagonists are reversible competitive blockers of histamine at the $H_2$ receptors, particularly those in the gastric parietal cells. They are tolerated well with very few side effects. Loperamide is used to treat nonspecific diarrhea and chronic diarrhea associated from inflammatory bowel disease. It is available in the US as the OTC drug Imodium. It is generally well tolerated and penetrates the CNS poorly. It is generally well tolerated and has few side effects except for gastrointestinal ones which are similar to those seen in the disease states it is used to treat. Diphenhydramine is used primarily as an antihistamine. It is available OTC as Benadryl and found in many OTC allergy relief products. It has effects at both central and peripheral Histamine-1 ($H_1$) receptors. Common side effects include sedation, poor coordination and upset stomach. Ascorbic Acid, also known as Vitamin C, is available as a dietary supplement and is also used as a food preservative. It is also found in the normal human diet. Humans cannot make Vitamin C and once the body's needs are met, it is excreted unchanged. Even modest supplementation with Vitamin C causes an increase in urinary Vitamin C levels so the possibility of using it as a marker was explored. It is well tolerated even in high doses. Riboflavin, also known as Vitamin B2, is available as a dietary supplement and also found in the normal human diet. It has few toxic effects even at high doses and has been studied extensively as a marker of adherence.

Methods of Analyzing the Urine and Saliva Samples

Urine and saliva samples were sent to an independent laboratory for analysis. The laboratory was blinded to the dose of marker used, sequencing of the different markers and simulated nonadherence of the subjects.

Materials

Loperamide, Dextromethorphan (DXM), Ascorbic Acid and Diphenhydramine were purchased from the Cerilliant Corporation. Famotidine S Oxide, Ranitidine S Oxide, and Nizatidine N Oxide were purchased from Mulcan Corporation. Desmethyl Nizatidine and Nizatidine S Oxide were purchased from Toronto Research Chemicals. Famotidine and Nizatidine were purchased from Sigma Aldrich. Ranitidine was purchased in the form of the over the counter drug Zantac. Normeperidine Internal Standard, and ETS Internal Standard, and Morphine Internal Standard were purchased from the Cerrilliant Corporation. HPLC grade methyl alcohol, ammonium formate, and formic acid were purchased from Fisher Scientific. All $H_2$ blockers were dissolved in methanol to 1 mg/mL.

Reagent Preparation

Buffer A is comprised of water with 1.56 mM of methyl alcohol and 2.5 mM ammonium formate and 0.1% formic acid. Buffer B is comprised of methyl alcohol with 2.78 mM of water and 5 mM ammonium formate and 0.1% formic acid.

Calibration Preparation

Calibration standards were prepared by appropriately diluting Loperamide, Dextromethorphan, and Ascorbic Acid to produce Blank, 1000 ng/mL, and 10,000 ng/mL. Calibration Standards for Diphenhydramine included a 100,000 ng/mL standard. Calibration Standards were prepared by appropriately diluting the $H_2$ blockers to produce 1.6, 8.0, 40, 100, 200, 1000, 2000 ng/mL. They are then combined with a solution containing 400 uL Buffer A and 25 uL of Internal Standard Morphine diluted to 1000 ng/mL. Calibration Standards were prepared by appropriately diluting Riboflavin to produce 16, 80, 400, 1000, 2000, and 10,000 ng/mL. It is then combined with a solution containing 400 uL Buffer A and 25 uL of Internal Standard Morphine diluted to 1000 ng/mL.

Sample Preparation

Loperamide, Dextromethorphan, Diphenhydramine:
200 ul of urine was transferred to a vial and diluted with 400 ul of an aqueous solution containing 25 uL Internal Standard Normeperidine at 1000 ng/mL. Sample was mixed then centrifuged at 12,000 rpm for 6 minutes. An aliquot of supernatant was injected into LC-MS/MS system for analysis.

$H_2$ Blockers:
200 uL of urine was transferred to a vial and diluted with 400 uL of an aqueous solution containing 25 uL Internal Standard Morphine at 1000 ng/mL. Sample was mixed then centrifuged at 12,000 rpm for 6 minutes. An aliquot of supernatant was injected into LC-MS/MS system for analysis.

Riboflavin:
20 uL of urine was transferred to a vial and diluted with 580 uL of an aqueous solution containing 25 uL Internal Standard Morphine at 1000 ng/mL. Sample was mixed then centrifuged at 12,000 rpm for 6 minutes. An aliquot of supernatant was injected into LC-MS/MS system for analysis.

Ascorbic Acid:
200 ul of urine was transferred to a vial and diluted with 400 ul of an aqueous solution containing 25 uL IS ETS at 1000 ng/mL. Sample was mixed then centrifuged at 12,000 rpm for 6 minutes. An aliquot of supernatant was injected into LC-MS/MS system for analysis.

HPLC Operating Conditions

A Shimadzu SIL series LC system equipped with degasser, paired diaphragm pump (LC-20ADXR), column oven (CTO20A) along with auto sampler (SIL20ACHT) was used to inject an aliquot of the processed samples through a reverse phase LC Column which was maintained at 40±1 degree Celsius. A gradient elution comprised of Buffer A and Buffer B was delivered at flow rate of 0.8 mL/min.

Mass Spectrometry Operating Conditions

Quantitation was achieved by MS/MS detection for all analytes using an AB SCIEX Triple Quad-5500 mass spectrometer equipped with Turboionspray interface. Detection of the ions was performed in the multiple reaction monitoring (MRM) mode.

Results of Saliva Sample Analysis

The results of analyzing the saliva samples from four subjects A, B, C and D were averaged for days 1-8 and shown in the table below.

| Multiple Marker Experiment 1: Average of Saliva Samples, ng/mL | | | | | | | |
|---|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydramine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 30.725 | 85.525 |
| Day 2 | 16.8 | 0 | 0 | 0 | 0 | 33.61 | 92.025 |

| Multiple Marker Experiment 1: Average of Saliva Samples, ng/mL | | | | | | |
|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydramine 25 mg (Dosed Day 5) | Ascorbic Acid 1000 mg (Dosed Day 6) | Riboflavin 32 mg (Dosed Day 7) |
| Day 3 | 1.55725 | 0.43075 | 0 | 0 | 0 | 32.825 | 58.1925 |
| Day 4 | 0.56175 | 0.17975 | 8.404 | 0 | 0 | 33.275 | 45.5225 |
| Day 5 | 0.3665 | 0.25725 | 1.517 | 5.714 | 0 | 23.8 | 37.295 |
| Day 6 | 0.176 | 0.11175 | 0.5015 | 0.3395 | 227.15 | 36.225 | 85.503 |
| Day 7 | 0.07575 | 0.09225 | 0.43925 | 0 | 0 | 36.825 | 40.8375 |
| Day 8 | 0.048 | 0.0265 | 0.19725 | 0 | 0 | 27.025 | 43.0925 |

With the exception of ascorbic acid and riboflavin, markers were not detected at day one, confirming that markers were not present before the experiment began. Ascorbic Acid and riboflavin are present in the normal diet and so their presence would be expected at day 1. Additionally, for the markers not found in the normal diet (ranitidine, loperamide, dextromethorphan (DXM), famotidine, diphenhydramine) markers were not detected until after they were dosed, confirming that no outside sources of marker were inadvertently ingested before dosing in the experiment. All 7 markers were detected in saliva, but not in every subject. Diphenhydramine was not detectable in 2 of the 4 subjects, all of the other markers were able to be detected at least once in every subject. The levels which were detected in saliva were much lower than for urine and concentrations of parent drug exceeded metabolites. This is consistent with the characteristics of most compounds when saliva and urine are compared.

Conclusions of Saliva Sample Analysis

Combining what is generally known about the detection of substances in saliva and the results of the experiment above, the lack of consistency in detection of markers between subjects and the small window of detection prevents them from being easily used as long term markers of adherence. An individual marker however, could be used reliably as an easy way to spot check adherence without the difficulties of urine collection.

Results of Urine Sample Analysis

The results of analyzing the urine samples from four subjects A, B, C and D were averaged for days 1-8 and shown in the table below.

With the exception of ascorbic acid and riboflavin, markers were not detected at day one, confirming that markers were not present before the experiment began. Ascorbic Acid and Riboflavin are present in the normal diet and so their presence would be expected at day 1. Additionally, for the markers not found in the normal diet (ranitidine, loperamide, dextromethorphan (DXM), famotidine, diphenhydramine) markers were not detected until after they were dosed, confirming that no outside sources of marker were inadvertently ingested before dosing in the experiment. All 7 markers were detected in all four patients at day 8. Levels of ascorbic acid after dosing did not differ significantly from baseline levels (day 1-6). Levels of riboflavin after dosing differed slightly from baseline levels (day 1-7). Levels of the remaining markers (ranitidine, loperamide, dextromethorphan (DXM), famotidine, diphenhydramine) were zero before dosing, peaked the day after dosing and slowly decreased over time.

Conclusions of Urine Sample Analysis and Discussion of Suitability of Different Markers Combining what is generally known about the detection of substances in urine and the results of the experiment above, the consistency in detection of all markers in all subjects and the longer time window when they are detected makes them suitable as longer term markers of adherence. Riboflavin and ascorbic acid's presence in the diet limit their usefulness as markers. GI side effects of constipation and

| Multiple Marker Experiment 1: Average of Urine Samples ng/mL | | | | | | |
|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydramine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 1960 | 2242.25 |
| Day 2 | 3715.25 | 0 | 0 | 0 | 0 | 2098.75 | 2493.25 |
| Day 3 | 351 | 104.9 | 0 | 0 | 0 | 2260 | 2958.5 |
| Day 4 | 56.5 | 62.225 | 333 | 0 | 0 | 2656.25 | 5127.5 |
| Day 5 | 40.675 | 16.0625 | 27.475 | 1564.5 | 0 | 2033.25 | 2112.5 |
| Day 6 | 34.275 | 10.2475 | 7.6925 | 203.25 | 971500 | 1960.75 | 2270 |
| Day 7 | 13.8975 | 2.64375 | 2.41925 | 64.4975 | 162750 | 2559.25 | 3095.75 |
| Day 8 | 10.38 | 1.18225 | 1.487 | 43.18 | 88725 | 2096 | 5710 | stomach cramps with loperamine in normal subjects could confound a study's results or unblind subjects to the presence of marker compound being used. Diphenhydramine and dextromothorphan's use in many OTC cough cold and allergy preparations raises the chances for accidental exposure to the markers. The $H_2$ blockers ranitidine and famotidine overcome many of the other marker's problems: they are not found in the diet, have few side effects, are generally known to subjects and could be easily avoided in OTC products. In other experiments with the $H_2$ blockers, the dose, number of doses and sequence were able to be adjusted to come close to the ideal marker. Ultimately, acceptance of a marker's suitability for use depends upon the individual characteristics it displays experimentally and what is already known about its pharmacology, toxicity and safety.

Example 2B: Seven Marker Sequencing with Non-Adherence

In experiment 2, the same subjects, markers and methods were used as in experiment 1 except each subject skipped a randomly assigned marker dose to simulate a one day period of nonadherence. A 2 week washout period was used between experiments to prevent markers from experiment 1 from showing up or "bleeding over" into experiment 2. In experiment 2, subject A skipped ranitidine on Day 1, subject B skipped diphenhydramine on day 5, subject C skipped Loperamide on day 2, and subject D skipped dextromethorphan (DXM) on day 3.

Under usual conditions adherence would likely be monitored on a weekly basis with the goal of confirming 100% adherence for the previous week meaning that urine would be collected on day 8 not every day as shown in the examples below. Typically, the results would be shown on day 8 as "detected" or "not detected" for a specific marker with detection of all 7 markers confirming 100% adherence.

Daily urine collection and laboratory analysis was performed in experiments 1 and 2 to better understand the characteristics of each marker species. Results were compared for the same subject in both parts of the multimarker experiment in the tables below.

Results of Multiple Marker Experiment 2

Subject A's adherence with all markers in Experiment 1 was confirmed by finding all 7 markers at day 8 as noted in table below.

| Subject A, Urine Results, Experiment #1, Adherent with all Markers, ng/mL | | | | | | | |
|---|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydramine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 1335 | 1310 |
| Day 2 | 801 | 0 | 0 | 0 | 0 | 1146 | 343 |
| Day 3 | 156 | 28.4 | 0 | 0 | 0 | 2022 | 454 |
| Day 4 | 63.4 | 98.4 | 146 | 0 | 0 | 2628 | 4720 |
| Day 5 | 61.8 | 31.6 | 11.7 | 951 | 0 | 1045 | 3040 |
| Day 6 | 58.5 | 24.1 | 3.6 | 239 | 2020000 | 1511 | 1720 |
| Day 7 | 11.2 | 0.035 | 0.987 | 2.39 | 171000 | 2801 | 733 |
| Day 8 | 1.16 | 0.022 | 0.341 | 1.12 | 55800 | 1598 | 1340 |

Subject A's results in the table below suggest nonadherence on day 1 by the absence of ranitidine on day 8. The presence of all other markers as expected confirms adherence on days 2-7.

| Subject A, Urine Results, Experiment #2, Non-Adherence Simulated by Skipping Day 1 of Ranitidine, ng/mL | | | | | | | |
|---|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydramine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 546 | 1410 |
| Day 2 | 0 | 0 | 0 | 0 | 0 | 4639 | 738 |
| Day 3 | 0 | 93.1 | 0 | 0 | 0 | 4406 | 417 |
| Day 4 | 0 | 53.1 | 81.1 | 0 | 0 | 6113 | 581 |
| Day 5 | 0 | 20.7 | 8.67 | 9370 | 0 | 3531 | 1560 |
| Day 6 | 0 | 6.16 | 3.46 | 364 | 481000 | 845 | 1420 |
| Day 7 | 0 | 2.47 | 0.456 | 21.2 | 239000 | 2925 | 896 |
| Day 8 | 0 | 1.48 | 0.194 | 6.61 | 130000 | 4877 | 6720 |

Subject B's adherence with all markers in Experiment 1 was confirmed by finding all 7 markers at day 8 as noted in table below.

| | Subject B, Urine Results, Experiment #1, Adherent with all Markers, ng/mL | | | | | | |
|---|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydra-mine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 1048 | 5630 |
| Day 2 | 4220 | 0 | 0 | 0 | 0 | 2354 | 3400 |
| Day 3 | 456 | 206 | 0 | 0 | 0 | 1445 | 3040 |
| Day 4 | 42.8 | 26.8 | 358 | 0 | 0 | 2679 | 8310 |
| Day 5 | 19.6 | 6.94 | 31.4 | 519 | 0 | 2317 | 2450 |
| Day 6 | 16.4 | 5.5 | 17.8 | 149 | 663000 | 1496 | 3560 |
| Day 7 | 5.19 | 2.33 | 3.96 | 96.3 | 151000 | 1777 | 4000 |
| Day 8 | 4.76 | 0.107 | 3.56 | 73.3 | 120000 | 1872 | 8270 |

Subject B's results in the table below suggest nonadherence on day 5 by the absence of diphenhydramine on day 8. The presence of all other markers as expected confirms adherence on days 1-4 and 6-7.

| | Subject B, Urine Results, Experiment #2, Non-Adherence Simulated by Skipping Day-5 of Diphenhydramine, ng/mL | | | | | | |
|---|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydra-mine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 2660 | 2000 |
| Day 2 | 8260 | 0 | 0 | 0 | 0 | 3353 | 1980 |
| Day 3 | 443 | 209 | 0 | 0 | 0 | 2501 | 3150 |
| Day 4 | 181 | 101 | 2640 | 0 | 0 | 3736 | 2740 |
| Day 5 | 92 | 32.3 | 181 | 4210 | 0 | 4501 | 2950 |
| Day 6 | 44 | 13.8 | 14.7 | 1200 | 0 | 3689 | 3200 |
| Day 7 | 42 | 12.8 | 16.6 | 1140 | 0 | 2945 | 8980 |
| Day 8 | 35.5 | 2.92 | 2.63 | 33.5 | 0 | 3311 | 3390 |

Subject C's adherence with all markers in Experiment 1 was confirmed by finding all 7 markers at day 8 as noted in table below.

| | Subject C, Urine Results, Experiment #1, Adherent with all Markers, ng/m | | | | | | |
|---|---|---|---|---|---|---|---|
| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydra-mine 25 mg (Dosed Day 5) | Ascorbic Acid 1000 mg (Dosed Day 6) | Riboflavin 32 mg (Dosed Day 7) |
| Day 1 | 0 | 0 | 0 | 0 | 0 | 1290 | 1210 |
| Day 2 | 4930 | 0 | 0 | 0 | 0 | 2106 | 4940 |
| Day 3 | 492 | 75.2 | 0 | 0 | 0 | 1947 | 3150 |
| Day 4 | 68.3 | 23.7 | 187 | 0 | 0 | 1892 | 3150 |
| Day 5 | 41.9 | 7.11 | 15 | 968 | 0 | 2503 | 1230 |
| Day 6 | 39.6 | 5.02 | 4.84 | 165 | 618000 | 1812 | 1680 |
| Day 7 | 25.2 | 2.41 | 2.12 | 122 | 144000 | 1751 | 4450 |
| Day 8 | 23.5 | 1.89 | 0.787 | 78.9 | 125000 | 2020 | 9920 |

Subject C's results in the table below suggest nonadherence on day 2 by the absence of Loperamide on day 8. The presence of all other markers as expected confirms adherence on days 1 and 3-7.

Subject C, Urine Results, Experiment #2, Non-adherence Simulated by Skipping Day-2 of Loperamide, ng/mL

| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydra-mine 25 mg (Dosed Day 5) | Ascorbic Acid 1000 mg (Dosed Day 6) | Riboflavin 32 mg (Dosed Day 7) |
|---|---|---|---|---|---|---|---|
| Day 1 | 0 | 0 | 0 | 0 | 0 | 1868 | 1160 |
| Day 2 | 7640 | 0 | 0 | 0 | 0 | 2488 | 540 |
| Day 3 | 994 | 0 | 0 | 0 | 0 | 4544 | 1400 |
| Day 4 | 353 | 0 | 377 | 0 | 0 | 2519 | 2530 |
| Day 5 | 115 | 0 | 40 | 3830 | 0 | 5290 | 1660 |
| Day 6 | 64.9 | 0 | 1.35 | 429 | 151000 | 1035 | 1710 |
| Day 7 | 53.4 | 0 | 1.11 | 390 | 214000 | 1841 | 2340 |
| Day 8 | 23.9 | 0 | 0.15 | 139 | 8840 | 1609 | 2150 |

Subject D's adherence with all markers in Experiment 1 was confirmed by finding all 7 markers at day 8 as noted in table below.

Subject D, Urine Results, Experiment #1, adherent with all Markers, ng/m

| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydra-mine 25 mg (Dosed Day 5) | Ascorbic Acid 1000 mg (Dosed Day 6) | Riboflavin 32 mg (Dosed Day 7) |
|---|---|---|---|---|---|---|---|
| Day 1 | 0 | 0 | 0 | 0 | 0 | 4167 | 819 |
| Day 2 | 4910 | 0 | 0 | 0 | 0 | 2789 | 1290 |
| Day 3 | 300 | 110 | 0 | 0 | 0 | 3626 | 5190 |
| Day 4 | 51.5 | 100 | 641 | 0 | 0 | 3426 | 4330 |
| Day 5 | 39.4 | 18.6 | 51.8 | 3820 | 0 | 2268 | 1730 |
| Day 6 | 22.6 | 6.37 | 4.53 | 260 | 585000 | 3024 | 2120 |
| Day 7 | 14 | 5.8 | 2.61 | 37.3 | 185000 | 3908 | 3200 |
| Day 8 | 12.1 | 2.71 | 1.26 | 19.4 | 54100 | 2894 | 3310 |

Subject D's results in the table below suggest nonadherence on day 3 by the absence of Dextromethorphan (DXM) on day 8. The presence of all other markers as expected confirms adherence on days 1-2 and 4-7.

Subject D, Urine Results, Experiment #2, Non-adherence Simulated by Skipping Day-3 of Dextromethorphan (DXM), ng/mL

| Day | Ranitidine 150 mg (Dosed Day 1) | Loperamide 2 mg (Dosed Day 2) | DXM 30 mg (Dosed Day 3) | Famotidine 20 mg (Dosed Day 4) | Diphenhydra-mine 25 mg (Dosed Day 5) | Ascorbic Acid 1000 mg (Dosed Day 6) | Riboflavin 32 mg (Dosed Day 7) |
|---|---|---|---|---|---|---|---|
| Day 1 | 0 | 0 | 0 | 0 | 0 | 5071 | 517 |
| Day 2 | 6630 | 0 | 0 | 0 | 0 | 4719 | 946 |
| Day 3 | 1030 | 35.7 | 0 | 0 | 0 | 4905 | 2350 |
| Day 4 | 237 | 68.1 | 0 | 0 | 0 | 4926 | 3700 |
| Day 5 | 131 | 18.5 | 0 | 5050 | 0 | 5020 | 2470 |
| Day 6 | 31.2 | 13.5 | 0 | 1670 | 684000 | 4404 | 1990 |
| Day 7 | 25.1 | 10.2 | 0 | 337 | 230000 | 5099 | 6170 |
| Day 8 | 2.77 | 2.84 | 0 | 27.8 | 75300 | 4324 | 3650 |

With the exception of ascorbic acid and riboflavin, markers were not detected at day one, confirming that markers were not present before the experiment began. Ascorbic Acid and Riboflavin are present in the normal diet and so their presence would be expected at day 1. Additionally, for the markers not found in the normal diet (ranitidine, loperamide, dextromethorphan (DXM), famotidine, diphenhydramine) markers were not detected until after they were dosed, confirming that no outside sources of marker were inadvertently ingested before dosing in the experiment. Levels of ascorbic acid after dosing did not differ significantly from baseline levels (day 1-6). Levels of riboflavin after dosing differed slightly from baseline levels (day 1-7). Levels of the remaining markers (ranitidine, loperamide, dextromethorphan (DXM), famotidine, diphenhydramine) were zero before dosing, peaked the day after dosing and slowly decreased over time. When marked were skipped to simulate nonadherence, they were not detected at any time during the experiment.

Conclusions of Experiment 2A

Combining what is generally known about the detection of substances in urine and the results of experiment 1 and 2 above, it can be seen that most of the markers are suitable as predictors of both adherence and nonadherence. Riboflavin and ascorbic acid's presence in the diet limit their usefulness as markers as they are detected even when not ingested. Further, for riboflavin and ascorbic acid, the great variability in levels between subjects and even the same subject at different times makes establishing a cutoff value difficult. It should be noted that absolute confirmation of nonadherence is difficult as absence of a marker on laboratory testing could occur from physiological or technical reasons even if the marker was ingested.

What is claimed is:

1. A method for monitoring adherence of a subject to a dosing schedule, the method comprising:
providing a dose pack for the subject, the dose pack comprising a pair of a biomarkingly effective dose of a marker and a dose of an agent,
obtaining a sample from the subject, and
analyzing the sample for the presence or absence of the marker or a degradation product of the marker,
wherein the marker comprises a prescription or over-the-counter $H_2$ histamine receptor antagonist at a lower than prescription or over-the-counter dose for the $H_2$ histamine receptor antagonist, a metabolite thereof, or a degradation residue thereof and
wherein the marker and the agent are different.

2. The method of claim 1, wherein the pair is in the form of a unitary formulation.

3. The method of claim 2,
wherein the unitary formulation is a solid dose form comprising a coating and
wherein the coating comprises the marker.

4. The method of claim 2,
wherein the unitary formulation is a solid dose form comprising a capsule and
wherein the marker is in a particulate form disposed in the capsule.

5. The method of claim 2,
wherein the unitary formulation is a solid dose form comprising a layered tablet having a first layer and a second layer, and
wherein the first layer and the second layer of the solid dose form comprise the marker and the agent, respectively.

6. The method of claim 1, wherein the sample comprises a sample of urine, saliva, tears, sweat, blood, plasma, lymph fluid, mucous, or tissue.

7. The method of claim 1, wherein the sample is analyzed by liquid chromatography, an antibody or affinity based reagent, or mass spectroscopy.

8. The method of claim 1 further comprising providing the dosing schedule,
wherein the dosing schedule comprises one or more administration times for the administration of the pair to the subject according to the dosing schedule during a monitoring window.

9. The method of claim 1,
wherein the dose pack further comprises a second pair of a biomarkingly effective dose of a second marker and a dose of the agent.

10. The method of claim 9, wherein the dose pack is configured to isolate the pair and the second pair from one and another.

11. The method of claim 9, wherein the dose pack comprises one or more markings corresponding to an administration time for administration of the pair and the second pair.

12. The method of claim 9, wherein the marker of the pair and the second marker of the second pair are different.

13. The method of claim 1, where the agent is an active pharmaceutical ingredient.

14. The method of claim 1, wherein the $H_2$ histamine receptor antagonist is selected from the group consisting of ranitidine, nizatidine, famotidine, and combinations thereof.

15. The method of claim 14, wherein the $H_2$ histamine receptor antagonist is a combination of at least two of ranitidine, nizatidine, and famotidine.

* * * * *